(12) United States Patent
Brenner et al.

(10) Patent No.: US 11,534,496 B2
(45) Date of Patent: Dec. 27, 2022

(54) COMPOSITIONS AND METHODS RELATING TO T PERIPHERAL HELPER CELLS IN AUTOANTIBODY-ASSOCIATED CONDITIONS

(71) Applicant: The Brigham and Women's Hospital, Inc., Boston, MA (US)

(72) Inventors: Michael B. Brenner, Newton, MA (US); Deepak A. Rao, Jamaica Plain, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 344 days.

(21) Appl. No.: 16/308,088

(22) PCT Filed: Dec. 6, 2016

(86) PCT No.: PCT/US2016/065107
§ 371 (c)(1),
(2) Date: Dec. 7, 2018

(87) PCT Pub. No.: WO2017/213695
PCT Pub. Date: Dec. 14, 2017

(65) Prior Publication Data
US 2019/0298850 A1 Oct. 3, 2019

Related U.S. Application Data

(60) Provisional application No. 62/347,066, filed on Jun. 7, 2016.

(51) Int. Cl.
| | |
|---|---|
| *A61K 47/68* | (2017.01) |
| *A61P 19/02* | (2006.01) |
| *A61K 39/395* | (2006.01) |
| *A61K 45/06* | (2006.01) |
| *A61K 51/10* | (2006.01) |
| *A61K 51/12* | (2006.01) |
| *C07K 16/28* | (2006.01) |
| *C07K 16/46* | (2006.01) |
| *C12N 5/0783* | (2010.01) |
| *G01N 33/564* | (2006.01) |
| *G01N 33/569* | (2006.01) |

(52) U.S. Cl.
CPC ...... *A61K 47/6849* (2017.08); *A61K 39/3955* (2013.01); *A61K 45/06* (2013.01); *A61K 51/1027* (2013.01); *A61K 51/1033* (2013.01); *A61K 51/1203* (2013.01); *A61P 19/02* (2018.01); *C07K 16/2818* (2013.01); *C07K 16/2833* (2013.01); *C07K 16/2866* (2013.01); *C07K 16/468* (2013.01); *C12N 5/0636* (2013.01); *G01N 33/564* (2013.01); *G01N 33/56972* (2013.01); *C07K 2317/31* (2013.01); *C07K 2319/00* (2013.01); *G01N 2333/70539* (2013.01); *G01N 2333/70596* (2013.01); *G01N 2333/7158* (2013.01); *G01N 2800/102* (2013.01)

(58) Field of Classification Search
None
See application file for complete search history.

(56) References Cited

U.S. PATENT DOCUMENTS

| | | |
|---|---|---|
| 2013/0211049 A1 | 8/2013 | Neville et al. |
| 2014/0286918 A1 | 9/2014 | Dao et al. |

FOREIGN PATENT DOCUMENTS

| | | |
|---|---|---|
| CN | 103487572 A | 1/2014 |
| WO | WO 90/14835 A1 | 12/1990 |
| WO | WO 2014/204229 A2 | 12/2014 |
| WO | WO 2014/204229 A3 | 12/2014 |

OTHER PUBLICATIONS

Dennis et al., 2014, Arth. Res. Ther. vol. 16: 1-18.*
Chtanova et al., 2005, J. Immunol. vol. 175: 7837-7847.*
Hirose et al., 1990, J. Rheum. vol. 17: 18-23.*
Bruhl et al., 2001, Clin. Exp. Immunol. vol. 126: 551-559.*
Fang et al., 2016, Cell Reports vol. 14: 1218-1231.*
Perna, 2010, J. Immunol. 184, 1 page.*
Invitation to Pay Additional Fees mailed Feb. 3, 2017, in a connection with PCT/US2016/065107.
International Search Report and Written Opinion dated Apr. 10, 2017, in connection with PCT/US2016/065107.
International Preliminary Report on Patentability dated Dec. 20, 2018, in connection with PCT/US2016/065107.
Extended European Search Report dated Dec. 12, 2019, in connection with EP Patent Application No. 16904833.7.
Agata et al., Expression of the PD-1 antigen on the surface of stimulated mouse T and B lymphocytes. Int Immunol. May 1996;8(5):765-72. doi: 10.1093/intimm/8.5.765.
Chtanova et al., T follicular helper cells express a distinctive transcriptional profile, reflecting their role as non-Th1/Th2 effector cells that provide help for B cells. J Immunol. Jul. 1, 2004;173(1):68-78.doi:10.4049/jimmunol.173.1.68.
Chu et al., A preliminary study on the characterization of follicular helper T (Tfh) cells in rheumatoid arthritis synovium. Acta Histochem. Apr. 2014;116(3):539-43. doi: 10.1016/j.acthis.2013.10.009. Epub Nov. 25, 2013.
Crotty, Follicular helper CD4 T cells (TFH). Annu Rev Immunol. 2011;29:621-63. doi: 10.1146/annurev-immunol-031210-101400. Abstract Only.

(Continued)

*Primary Examiner* — Amy E Juedes
(74) *Attorney, Agent, or Firm* — Wolf, Greenfield & Sacks, P.C.

(57) ABSTRACT

This disclosure provides methods and compositions for detecting Tph cells and/or reducing the number (or frequency) and/or activity of such cells in order to provide therapeutic benefit to a subject having or at risk of developing an autoantibody-associated condition such as an autoantibody-associated autoimmune disease.

18 Claims, 12 Drawing Sheets
Specification includes a Sequence Listing.

(56) References Cited

OTHER PUBLICATIONS

Haringman et al., Chemokine and chemokine receptor expression in paired peripheral blood mononuclear cells and synovial tissue of patients with rheumatoid arthritis, osteoarthritis, and reactive arthritis. Ann Rheum Dis. Mar. 2006;65(3):294-300. doi: 10.1136/ard.2005.037176. Epub Aug. 17, 2005.
Hatachi et al., CD4+ PD-1+ T cells accumulate as unique anergic cells in rheumatoid arthritis synovial fluid. J Rheumatol. Jul. 2003;30(7):1410-9.
Humby et al., Ectopic lymphoid structures support ongoing production of class-switched autoantibodies in rheumatoid synovium. PLoS Med. Jan. 13, 2009;6(1):e1. doi: 10.1371/journal.pmed.0060001.
James et al., Citrulline-specific Th1 cells are increased in rheumatoid arthritis and their frequency is influenced by disease duration and therapy. Arthritis Rheumatol. Jul. 2014;66(7):1712-22. doi: 10.1002/art.38637.
Katschke et al., Differential expression of chemokine receptors on peripheral blood, synovial fluid, and synovial tissue monocytes/macrophages in rheumatoid arthritis. Arthritis Rheum. May 2001;44(5):1022-32. doi: 10.1002/1529-0131(200105)44:5<1022::AID-ANR181>3.0.CO;2-N.
Kenefeck et al., Follicular helper T cell signature in type 1 diabetes. J Clin Invest. Jan. 2015;125(1):292-303. doi: 10.1172/JCI76238. Epub Dec. 8, 2014.
Kobayashi et al., A distinct human CD4+ T cell subset that secretes CXCL13 in rheumatoid synovium. Arthritis Rheum. Dec. 2013;65(12):3063-72. doi: 10.1002/art.38173.
Kugyelka et al., Enigma of IL-17 and Th17 Cells in Rheumatoid Arthritis and in Autoimmune Animal Models of Arthritis. Mediators Inflamm. 2016;2016:6145810. doi: 10.1155/2016/6145810. Epub Jan. 20, 2016.
Liarski et al., Cell distance mapping identifies functional T follicular helper cells in inflamed human renal tissue. Sci Transl Med. Apr. 2, 2014;6(230):230ra46. doi: 10.1126/scitranslmed.3008146.
Locci et al., Human circulating PD-1+CXCR3-CXCR5+ memory Tfh cells are highly functional and correlate with broadly neutralizing HIV antibody responses. Immunity. Oct. 17, 2013;39(4):758-69. doi: 10.1016/j.immuni.2013.08.031. Epub Sep. 12, 2013.
Ma et al., Increased frequency of circulating follicular helper T cells in patients with rheumatoid arthritis. Clin Dev Immunol. 2012;2012:827480. doi: 10.1155/2012/827480. Epub May 10, 2012.
Manzo et al., Mature antigen-experienced T helper cells synthesize and secrete the B cell chemoattractant CXCL13 in the inflammatory environment of the rheumatoid joint. Arthritis Rheum. Nov. 2008;58(11):3377-87. doi: 10.1002/art.23966.
Pitzat Is et al., New learnings on the pathophysiology of RA from synovial biopsies. Curr Opin Rheumatol. May 2013;25(3):334-44. doi: 10.1097/BOR.0b013e32835fd8eb. Abstract Only.
Qin et al., The chemokine receptors CXCR3 and CCR5 mark subsets of T cells associated with certain inflammatory reactions. J Clin Invest. Feb. 15, 1998;101(4):746-54. doi: 10.1172/JCI1422.
Raptopoulou et al., The programmed death 1/programmed death ligand 1 inhibitory pathway is up-regulated in rheumatoid synovium and regulates peripheral T cell responses in human and murine arthritis. Arthritis Rheum. Jul. 2010;62(7):1870-80. doi: 10.1002/art.27500.
Takemura et al., Lymphoid neogenesis in rheumatoid synovitis. J Immunol. Jul. 15, 2001; 167(2):1072-80. doi: 10.4049/jimmunol.167.2.1072.
Vinuesa et al., Follicular B helper T cells in antibody responses and autoimmunity. Nat Rev Immunol. Nov. 2005;5(11):853-65. Review.
Weinstein et al., Global transcriptome analysis and enhancer landscape of human primary T follicular helper and T effector lymphocytes. Blood. Dec. 11, 2014;124(25):3719-29. doi: 10.1182/blood-2014-06-582700. Epub Oct. 20, 2014.
Yu et al., Follicular helper T cells in rheumatoid arthritis. Clin Rheumatol. Sep. 2015;34(9):1489-93. doi: 10.1007/s10067-015-3028-5. Epub Jul. 31, 2015. Abstract Only.
PCT/US2016/065107, Feb. 3, 2017, Invitation to Pay Additional Fees.
PCT/US2016/065107, Apr. 10, 2017, International Search Report and Written Opinion.
PCT/US2016/065107, Dec. 20, 2018, International Preliminary Report on Patentability.
EP16904833.7, Dec. 12, 2019, Extended European Search Report.
Bocharnikov et al., Accelerating Medicines Partnership (AMP) RA/SLE Network. PD-1hiCXCR5—T peripheral helper cells promote B cell responses in lupus via MAF and IL-21. JCI Insight. Oct. 17, 2019;4(20):e130062. doi: 10.1172/jci.insight.130062.
Crotty, Follicular helper CD4 T cells (TFH). Annu Rev Immunol. 2011;29:621-63. doi: 10.1146/annurev-immunol-031210-101400.
Pitzalis et al., New learnings on the pathophysiology of RA from synovial biopsies. Curr Opin Rheumatol. May 2013;25(3):334-44. doi: 10.1097/BOR.0b013e32835fd8eb.
Yu et al., Follicular helper T cells in rheumatoid arthritis. Clin Rheumatol. Sep. 2015;34(9):1489-93. doi: 10.1007/s10067-015-3028-5. Epub Jul. 31, 2015.

\* cited by examiner

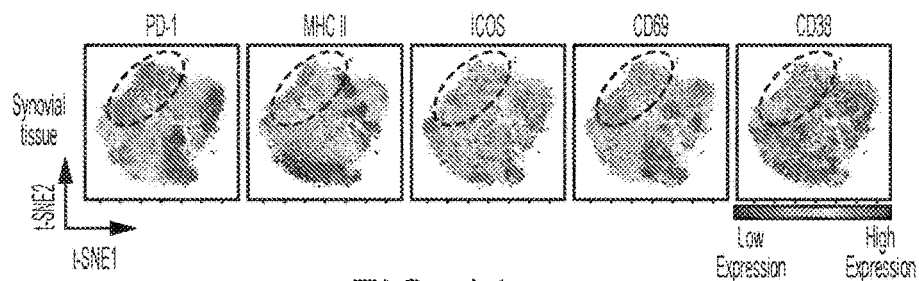
FIG. 1A
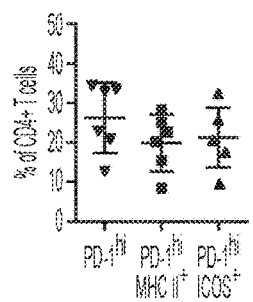
FIG. 1B
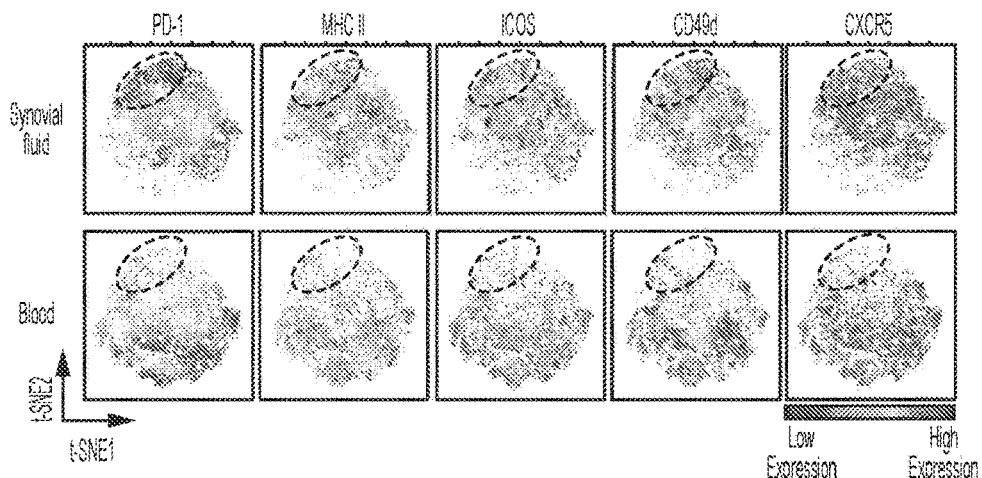
FIG. 1C
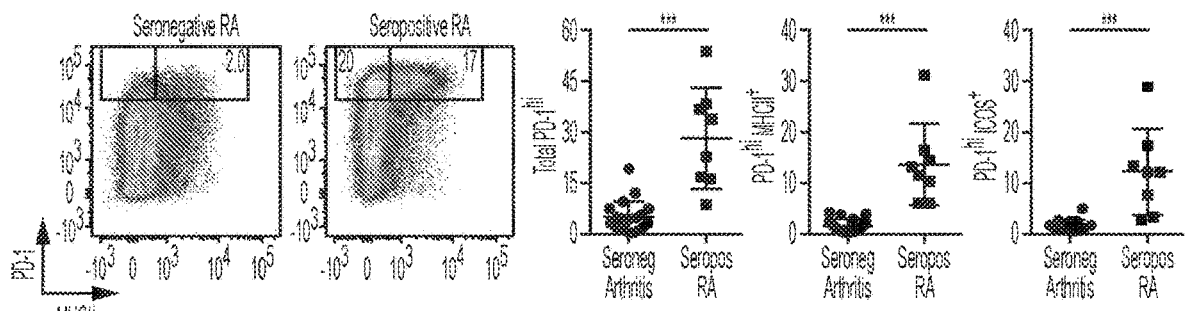
FIG. 1D
FIG. 1E
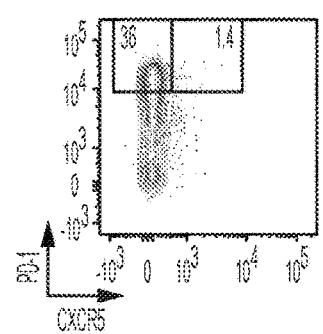
FIG. 1F
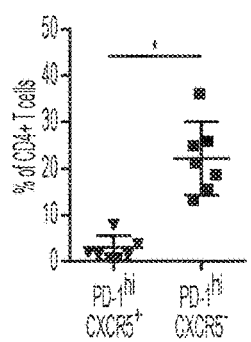
FIG. 1G

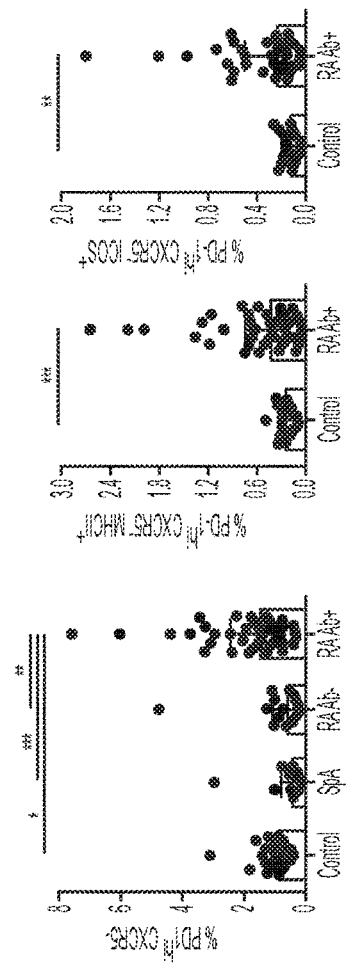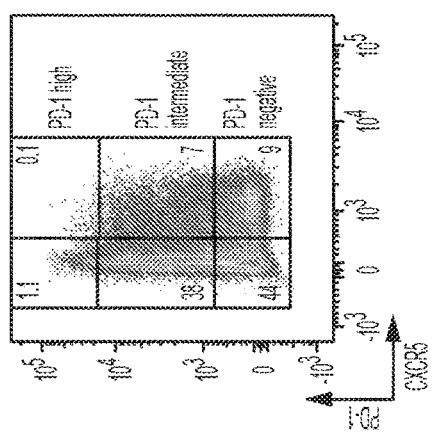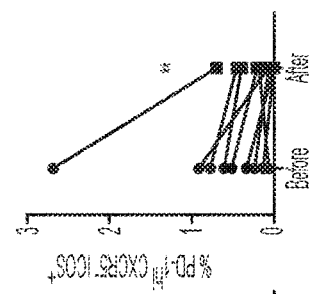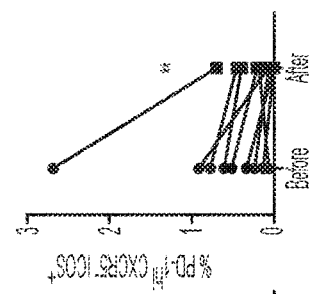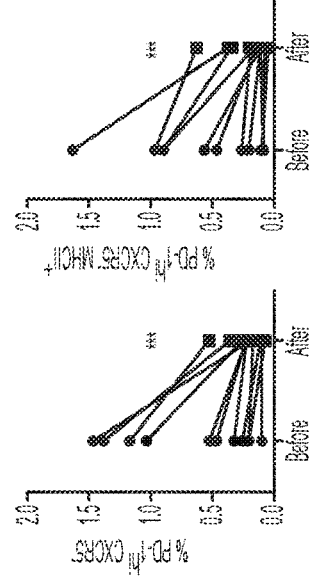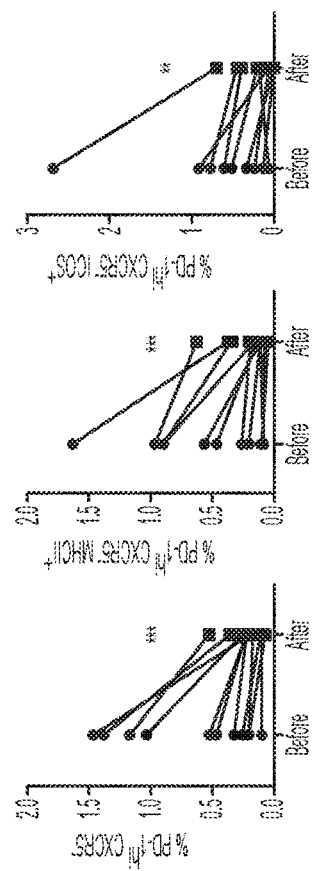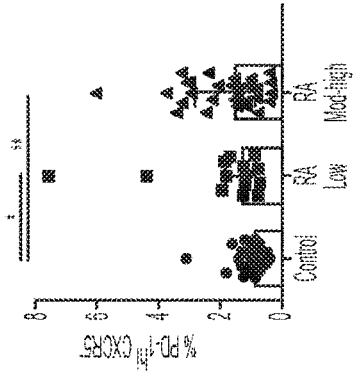
FIG. 2A  FIG. 2B  FIG. 2C  FIG. 2D  FIG. 2E

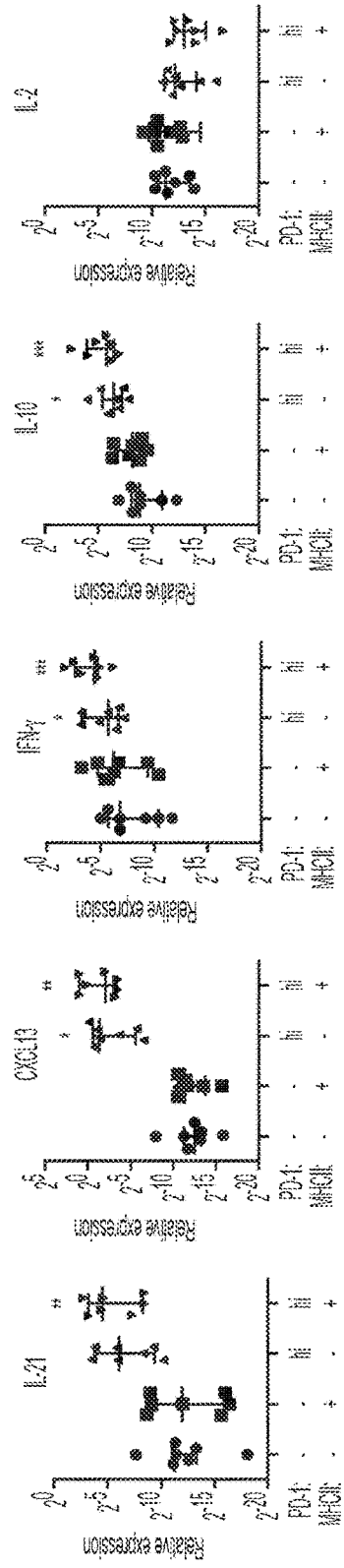
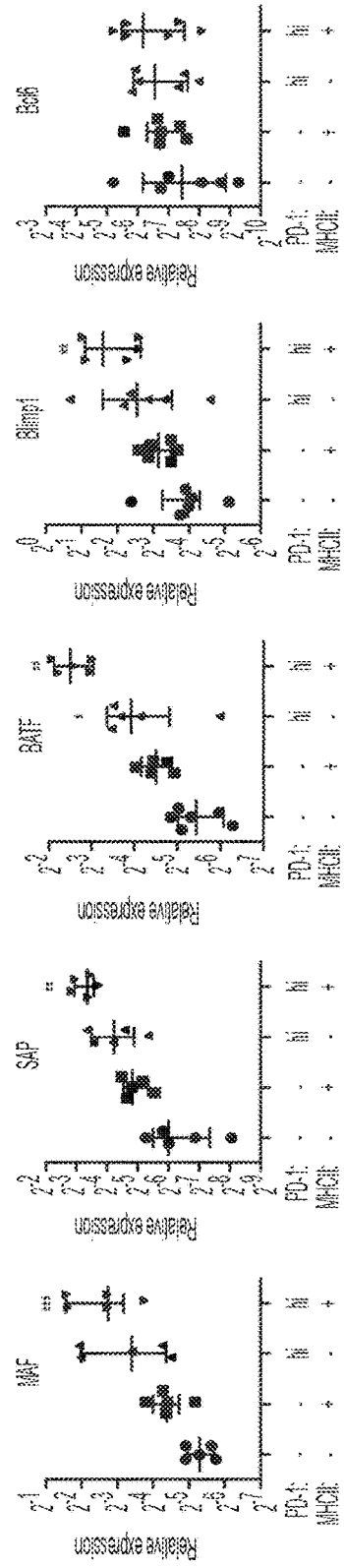
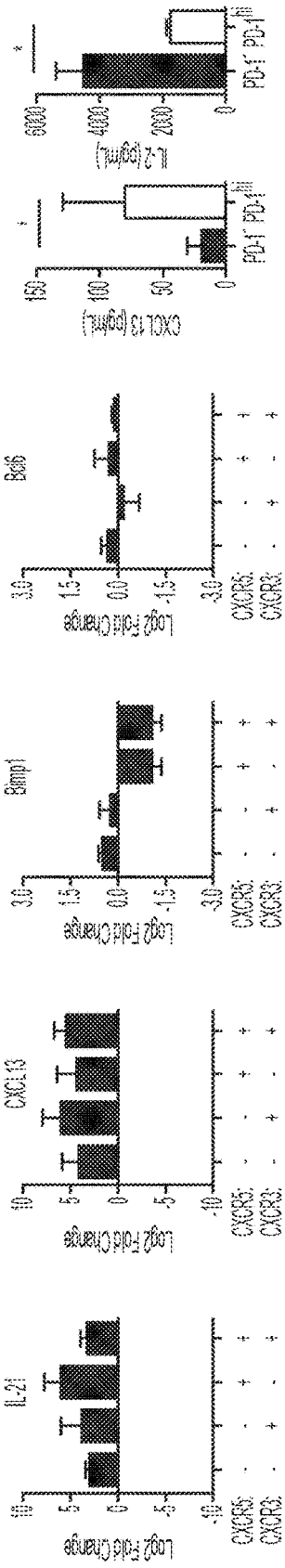
FIG. 3A
FIG. 3B
FIG. 3C
FIG. 3D

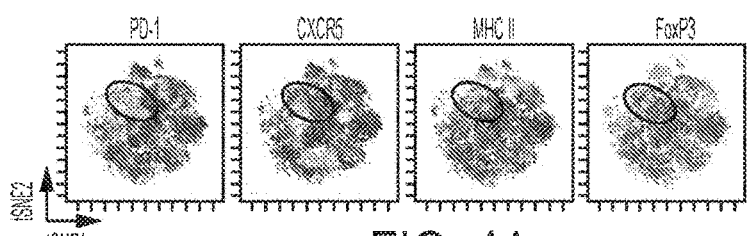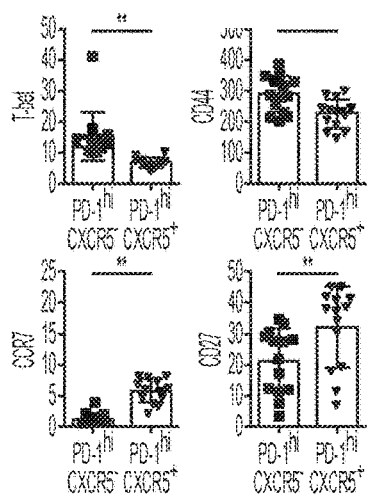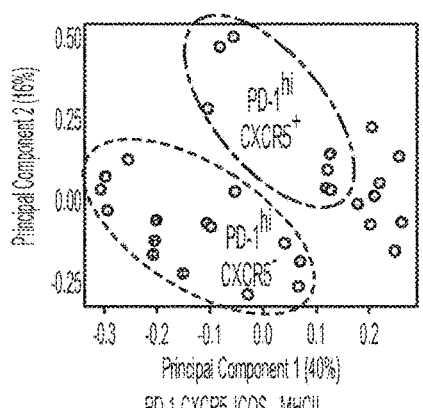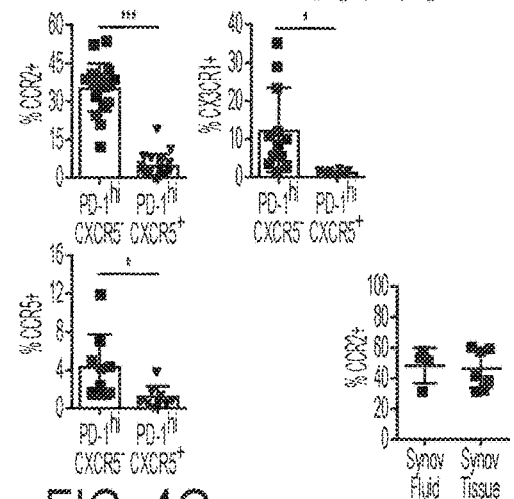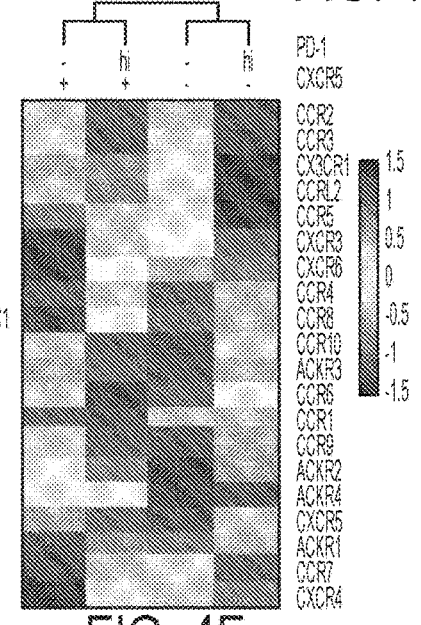
FIG. 4A  FIG. 4B  FIG. 4C  FIG. 4D  FIG. 4E  FIG. 4F  FIG. 4G  FIG. 4H

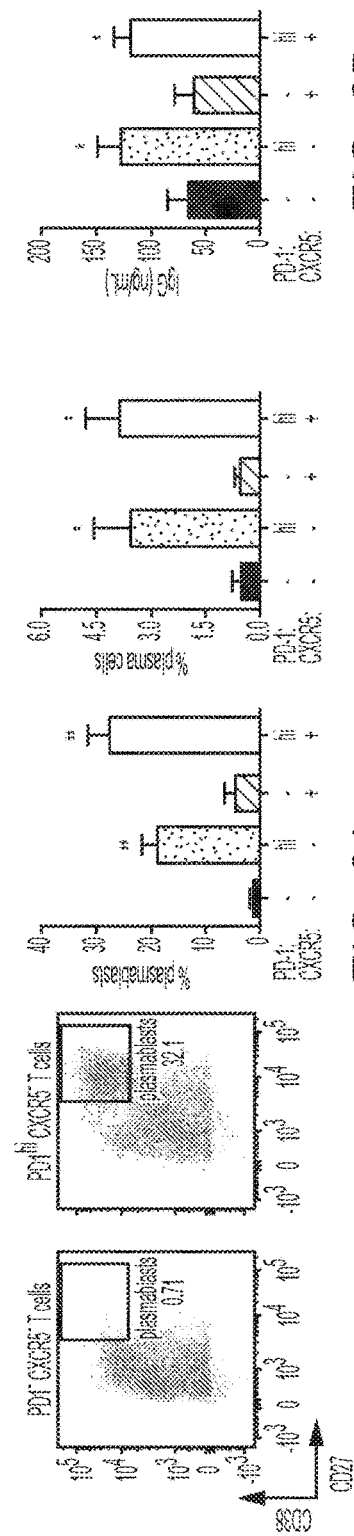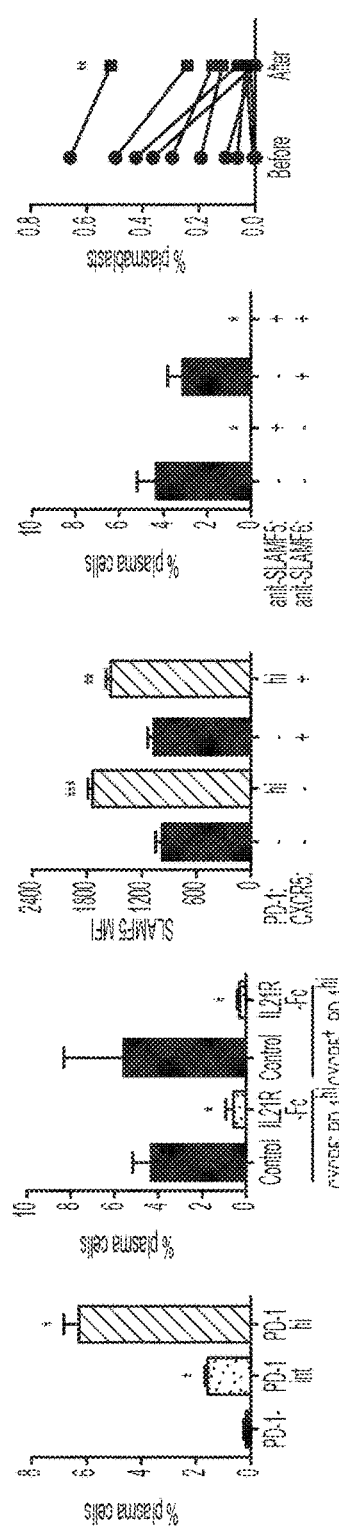

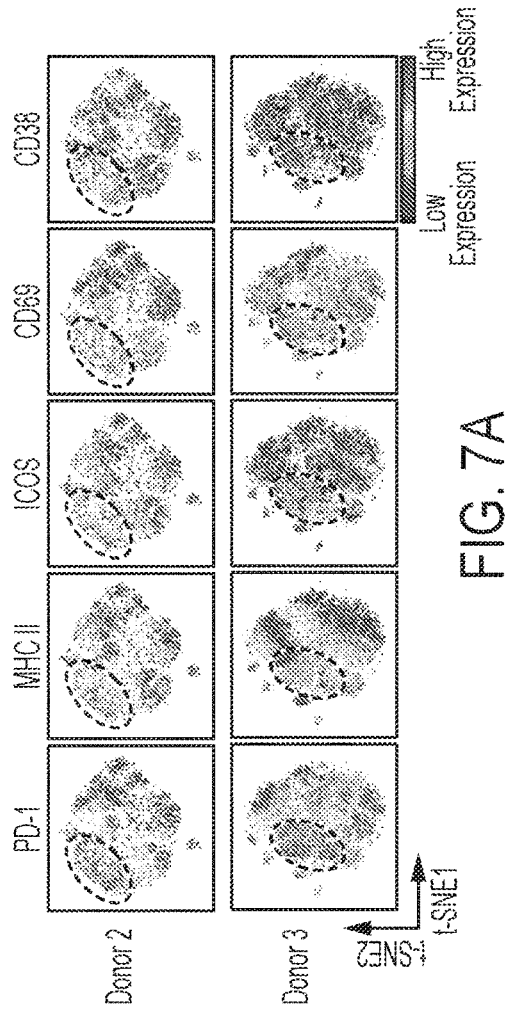
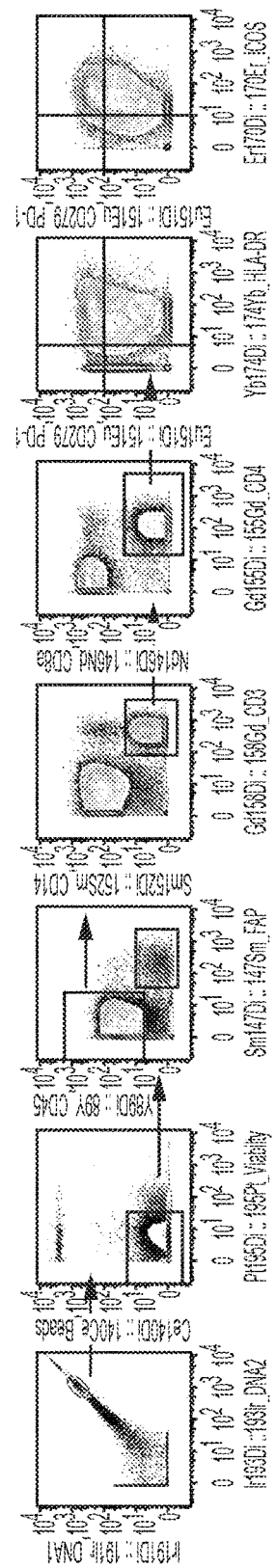
FIG. 7A
FIG. 7B

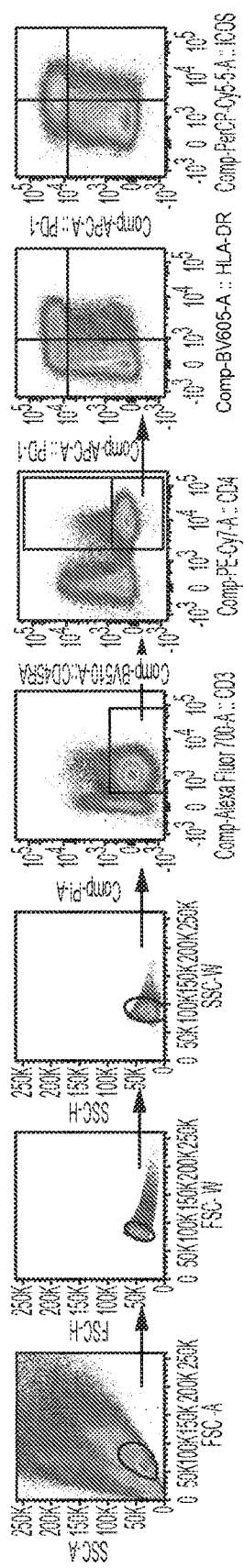
FIG. 7C
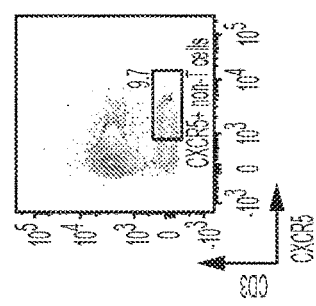
FIG. 7D
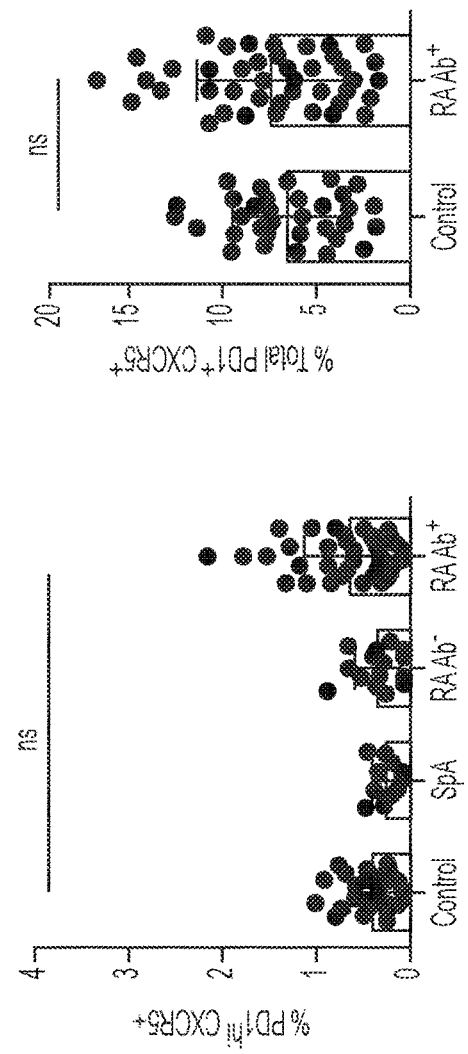
FIG. 8A
FIG. 8B

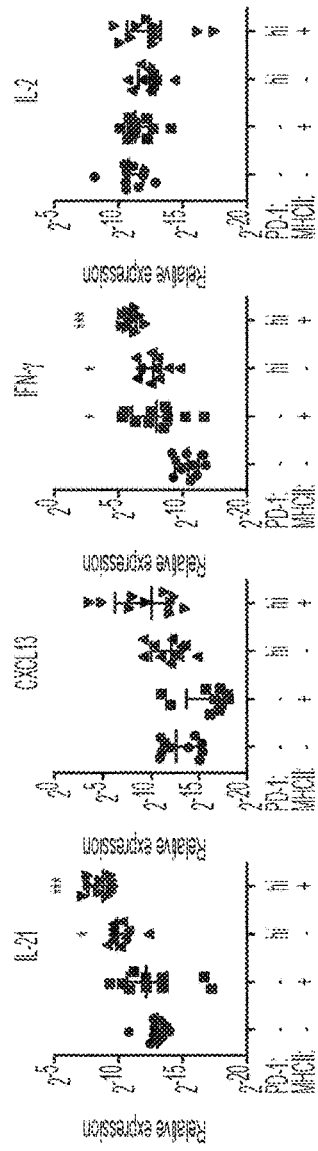
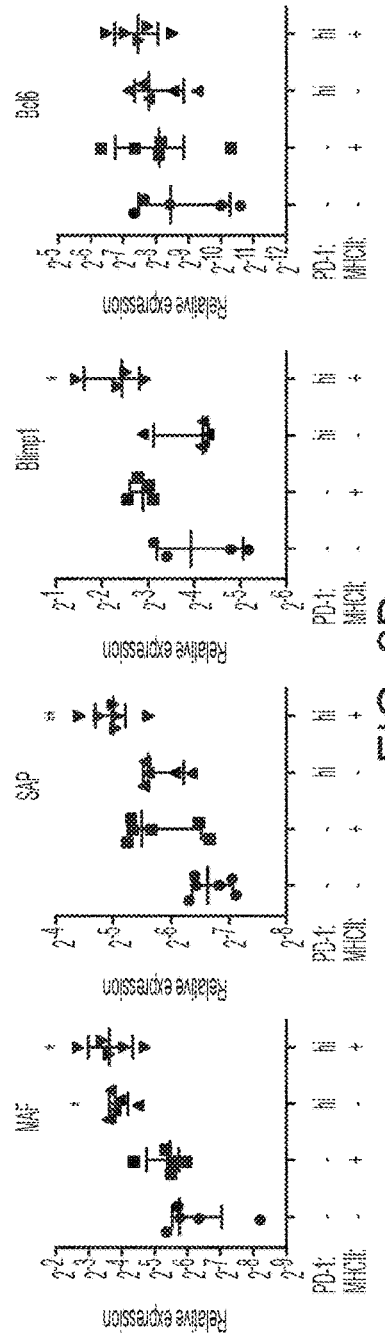
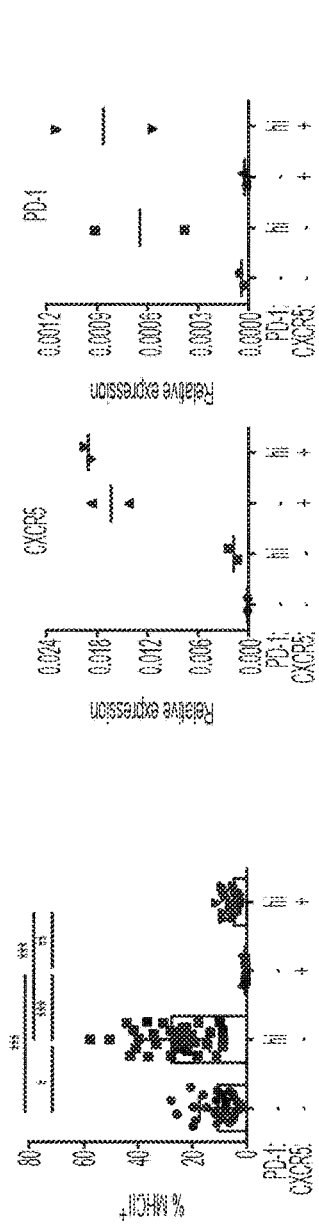
FIG. 9A
FIG. 9B
FIG. 9C
FIG. 9D

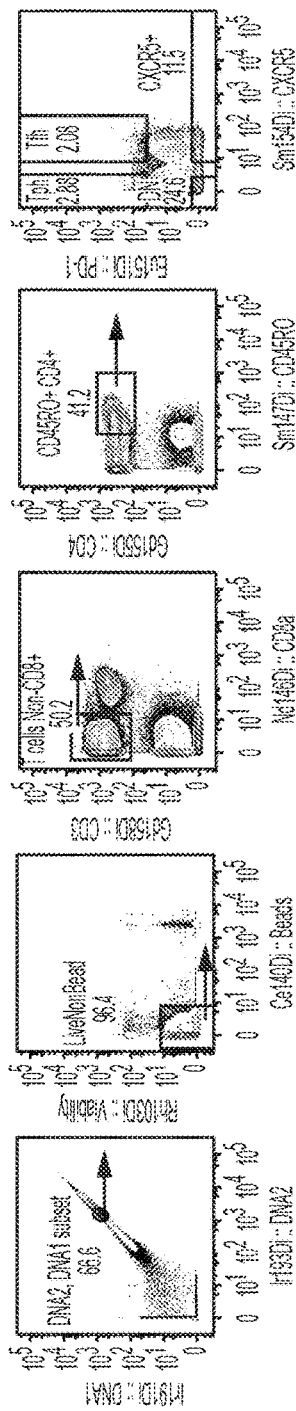
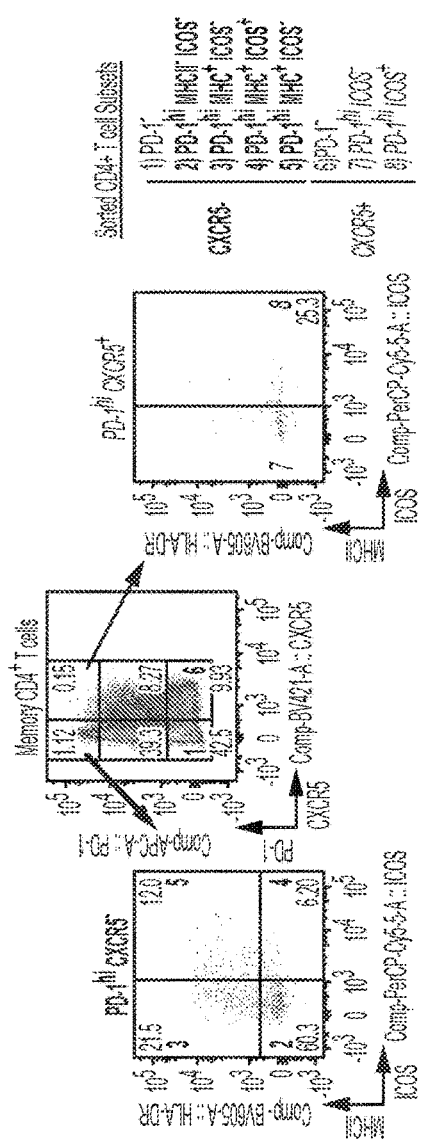
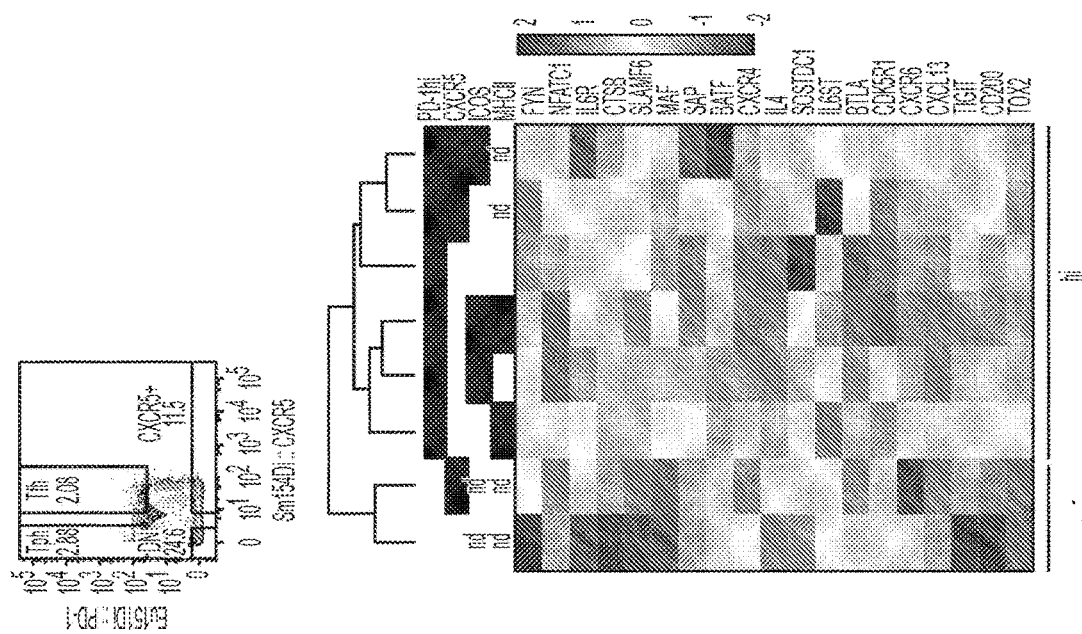
FIG. 10A
FIG. 10B
FIG. 10C

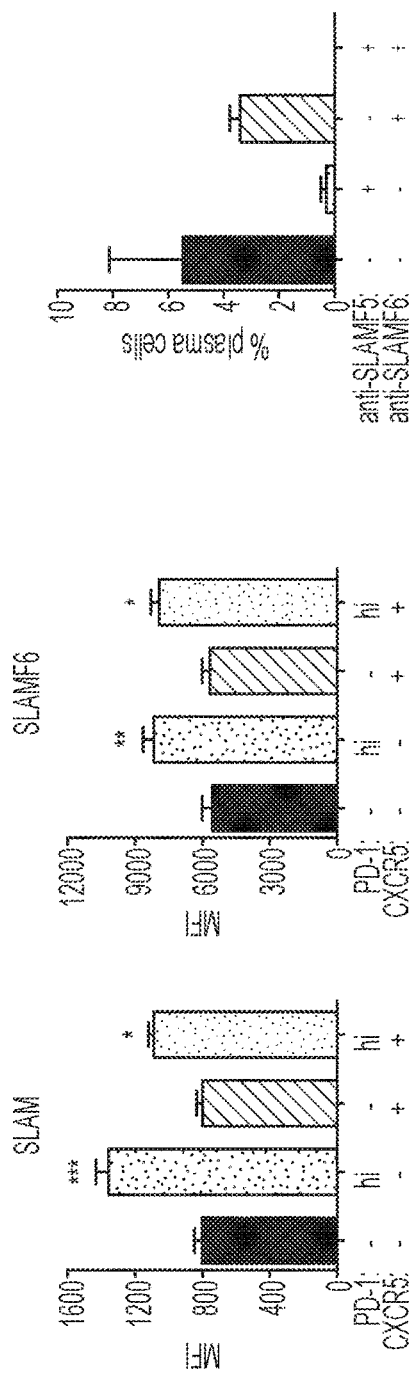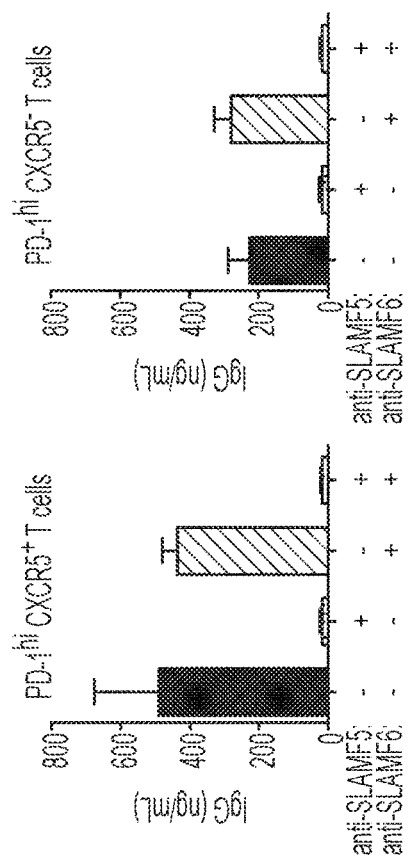
FIG. 11A
FIG. 11B
FIG. 11C

COMPOSITIONS AND METHODS RELATING TO T PERIPHERAL HELPER CELLS IN AUTOANTIBODY-ASSOCIATED CONDITIONS

RELATED APPLICATIONS

This application is a national stage filing under 35 U.S.C. § 371 of international application number PCT/US2016/065107, filed Dec. 6, 2016, which was published under PCT Article 21(2) in English and which claims the benefit under 35 U.S.C. § 119(e) of U.S. Provisional Application Ser. No. 62/347,066 entitled "COMPOSITIONS AND METHODS RELATING TO T PERIPHERAL HELPER CELLS IN AUTOANTIBODY-ASSOCIATED CONDITIONS" filed on Jun. 7, 2016, the entire contents of each of which are incorporated by reference herein.

FEDERALLY SPONSORED RESEARCH

This invention was made with U.S. Government support under grant number T32 AR007530-31 from the National Institutes of Health. The Government has certain rights to this invention.

BACKGROUND

Many autoimmune diseases are characterized by inappropriate T cell-B cell interactions and B cell production of autoantibodies, including rheumatoid arthritis (RA), systemic lupus erythematosus (SLE), multiple sclerosis, type I diabetes, and others.

CD4$^+$ T cells play a central role in mediating autoimmune pathology; however, identification of their key effector functions in specific autoimmune diseases remains elusive. Limited access to human tissues and incomplete knowledge of dominant auto-antigens are common barriers to characterization of autoantigen-specific human T cells in disease.

SUMMARY

This disclosure is based in part on the identification of a T helper cell population that is strikingly expanded in seropositive rheumatoid arthritis (RA) and in SLE. These cells have been termed peripheral helper T cells (Tph cells). It is contemplated that these cells support memory B cell responses in non-lymphoid tissues and act as drivers of pathologic B cell responses and autoantibody production.

In accordance with this disclosure, Tph cells have now been characterized CD4 positive (CD4+), PD-1$^{hi}$, and CXCR5 negative (CXCR5−), a feature that distinguishes them from follicular helper T cells (Tfh cells). Tph cells may also be CCR2 positive (CCR2+), CCR5 positive (CCR5+), and CX3CR1 positive (CX3CR1+), features that further distinguish them from Tfh cells. Tph cells may also be MHC Class II positive (MHCII+) and/or ICOS positive (ICOS+). As described herein, mass cytometry and transcriptional analyses demonstrated high IL-21, CXCL13, ICOS, and MAF expression. In addition, major differences were discovered between PD-1$^{hi}$ CXCR5$^-$ Tph cells and PD-1$^{hi}$ CXCR5$^+$ Tfh cells, including a distinct migratory program.

Tph cells are neither exhausted nor anergic. Rather, it has been shown in accordance with this disclosure that Tph cells provide help for B cells and thereby drive plasmablast differentiation. When tested functionally, Tph cells from synovial fluid or blood induced plasma cell differentiation in vitro via IL-21 and SLAMF5-interactions.

Also in accordance with this disclosure, Tph cells have been found in the synovium and in the blood of subjects having RA, and appear to be elevated in number, as compared to controls, at least in subjects having seropositive rheumatoid arthritis. Tph cell numbers are about 8-fold higher than Tfh cells (defined as PD-1$^{hi}$ CXCR5 positive (CXCR5+)) in synovial tissue of seropositive RA subjects. Surprisingly, Tph cells appear to be selectively expanded in the synovial fluid and blood of subjects having seropositive RA but not subjects having seronegative inflammatory arthritides such as seronegative RA, spondyloarthropathies, and juvenile idiopathic arthritis. Tph cells also have been found to be expanded in the blood of SLE subjects.

It was further found that the number or frequency of Tph cells correlated with disease activity. As described herein, subjects who experienced reduced disease activity after receiving a new RA therapy also had a lower frequency of Tph cells.

Accordingly, in view of these novel and surprising findings, provided herein are methods and compositions relating to Tph cells for monitoring and/or treating subjects having Tph-dependent autoimmune diseases including auto-antibody associated conditions such as but not limited to seropositive RA and SLE by depleting the number and/or suppressing the activity of Tph cells in such subjects. For example, provided herein are methods that aim to reduce the number and/or frequency of Tph cells in affected subjects, as may be accomplished using agents that selectively target and kill Tph cells. As described in greater detail herein, such depleting agents include those that target cytotoxic agents to Tph cells but not to other cells, based for example on single marker expression (e.g., high expression of PD-1) or combined marker expression (e.g., PD-1 and MHCII, or PD-1 and ICOS, etc.). In some instances, agents having bispecific binding activity are used to target cytotoxic agents selectively to Tph cells. Significantly, the agents are designed and/or selected based on their ability to bind to and deplete Tph cells. In some instances, the agents may accomplish this without activating Tph cells and without altering PD-1 signaling in such cells. In other instances, the agents may alter PD-1 signaling including down-regulating PD-1 signaling in Tph cells.

Also provided herein are methods that aim to inhibit or suppress the activity of Tph cells in affected subjects, as may be accomplished using agents that selectively inhibit Tph cells. As described in greater detail herein, such inhibitory agents include those that inhibit Tph cells but not other cells, based for example on single marker expression (e.g., high expression of PD-1) or combined marker expression (e.g., PD-1 and MHCII, or PD-1 and ICOS, etc.). In some instances, agents having bispecific binding activity are used to selectively inhibit Tph cells. Significantly, the agents may be designed and/or selected based on their ability to bind to and inhibit Tph cell activity, such as B cell helper activity. In some instances, the agents may alter PD-1 signaling including down-regulating PD-1 signaling in Tph cells.

Additional methods aim to monitor the presence or status of an autoimmune disease or the risk of developing an autoimmune disease, such as but not limited to an autoantibody-associated autoimmune diseases, as well as other autoantibody-associated conditions, in a subject by detecting Tph cells in a subject and optionally measuring the frequency of such Tph cells in the subject. The presence and/or frequency of Tph cells may be used to determine whether a subject is at risk of developing an autoimmune disease or an autoantibody-associated condition, has a previously undiagnosed autoimmune disease or an autoantibody-associated condition, and/or whether a subject is responsive or non-responsive to a therapy directed towards an autoimmune disease or an autoantibody-associated condition.

Still other methods aim to identify agents that selectively, including specifically, target and/or kill Tph cells, and/or assess the ability of agents to selectively, including specifically, target and/or kill Tph cells. Other methods aim to identify agents that selectively, including specifically, target and/or downregulate PD-1 signaling activity, and/or assess the ability of agents to selectively, including specifically, target and/or downregulate PD-1 signaling activity. Any of the foregoing methods may involve assessing the effect of the agent on the B cell helper activity of Tph cells.

Thus, provided herein, in one aspect, is a method for treating a subject having or at risk of having an autoimmune disease or an autoantibody-associated condition, the method comprising administering a therapeutically effective amount of an Tph cell depleting agent that is a conjugate of a Tph cell targeting agent and a cytotoxic agent and that specifically reduces Tph cell number.

In another aspect, provided herein is a method for treating a subject having or at risk of having seropositive rheumatoid arthritis, the method comprising administering a Tph cell depleting agent to a subject characterized as having an elevated level of circulating or synovial Tph cells, wherein the Tph cell depleting agent is a conjugate of a Tph cell targeting agent and a cytotoxic agent.

In another aspect, provided herein is a method for treating a subject having or at risk of having an autoimmune disease or an autoantibody-associated condition, the method comprising administering a therapeutically effective amount of an Tph cell inhibitory agent. In some embodiments, the Tph cell inhibitory agent binds to Tph cells, including to PD-1. In some embodiments, the Tph cell inhibitor agent binds to PD-1 modulates PD-1 signaling. The agent may be delivered in an amount that reduces Tph cell activity, including B cell helper activity, which may be assessed by level or frequency of Tph cells or by level of autoantibodies in the subject.

Various non-limiting embodiments are contemplated for the foregoing aspects. These are recited below.

In some embodiments, the subject has or is at risk of having seropositive rheumatoid arthritis.

In some embodiments, the Tph cells are circulating (e.g., detectable in a blood sample). In some embodiments, the Tph cells are synovial (e.g., detectable in synovial fluid or tissue).

In some embodiments, the Tph cell depleting agent or the Tph cell inhibitory agent comprises a PD-1 binding agent. In some embodiments, the Tph cell depleting agent or the Tph cell inhibitory agent comprises a bispecific targeting agent. In some embodiments, the Tph cell depleting agent or the Tph cell inhibitory agent comprises a bispecific targeting agent that binds to PD-1 and MHC class II. In some embodiments, the Tph cell depleting agent or the Tph cell inhibitory agent comprises a bispecific targeting agent that binds to PD-1 and ICOS. In some embodiments, the Tph cell depleting agent or the Tph cell inhibitory agent comprises a bispecific targeting agent that binds to PD-1 and CCR2. In some embodiments, the Tph cell depleting agent or the Tph cell inhibitory agent comprises a bispecific targeting agent that binds to PD-1 and CCR5.

In some embodiments, the Tph cell depleting agent or the Tph cell inhibitory agent comprises a bispecific targeting agent that binds to PD-1 and CX3CR1. The foregoing agents may be multi-specific agents and thus may bind to another Tph cell surface marker in addition to those recited.

In some embodiments, the bispecific targeting agent binds to MHC class II and at least one of PD-1, ICOS, CCR2, CCR5 or CX3CR1. In some embodiments, the bispecific targeting agent binds to ICOS and at least one of PD-1, MHC class II, CCR2, CCR5 or CX3CR1. In some embodiments, the bispecific targeting agent binds to CCR2 and at least one of PD-1, MHC class II, ICOS, CCR5 or CX3CR1. In some embodiments, the bispecific targeting agent binds to CCR5 and at least one of PD-1, MHC class II, ICOS, CCR2, or CX3CR1. In some embodiments, the bispecific targeting agent binds to CX3CR1 and at least one of PD-1, MHC class II, ICOS, CCR2 or CCR5. The foregoing agents may be multi-specific agents and thus may bind to three or more Tph cell surface markers as described herein.

In some embodiments, the bispecific targeting agent is a bispecific antibody or bispecific antibody fragment. In some embodiments, the bispecific targeting agent is a bispecific fusion protein.

In some embodiments, the cytotoxic agent is a toxin. In some embodiments, the cytotoxic agent is a radioisotope. In some embodiments, the cytotoxic agent is chemotherapeutic agent.

In some embodiments, the Tph cell targeting agent is identified by its ability to bind to cells that express high levels of PD-1 and not bind to cells that express intermediate levels of PD-1.

In some embodiments, the method further comprises administering one or more second therapeutic agents to the subject. In some embodiments, the one or more second therapeutic agents is an anti-inflammatory agent.

In some embodiments, the subject is a human. In some embodiments, the subject is an animal including but not limited to a companion animal such as a dog or cat. In some embodiments, the subject is an agricultural animal such as a horse.

Another aspect provides a method comprising immunodetecting Tph cells in a sample obtained from a subject, based on high expression of PD-1, expression of MHC Class II and/or ICOS, and expression of one or more of CCR2, CCR5 and CX3CR1.

In some embodiments, the method further comprises obtaining the sample from the subject. In some embodiments, the subject has not been diagnosed with rheumatoid arthritis. In some embodiments, the subject has rheumatoid arthritis. In some embodiments, the subject has seropositive rheumatoid arthritis.

In some embodiments, the subject has received a therapy. In some embodiments, the subject will receive a therapy. In some embodiments, the therapy comprises an anti-inflammatory agent.

In some embodiments, the sample is a whole blood sample or mononuclear blood cell sample. In some embodiments, the sample is a synovial fluid or tissue sample.

In some embodiments, the method further comprises quantitating Tph cell number or frequency in the sample.

In some embodiments, the Tph cells are immunodetected using anti-PD-1 antibody, anti-MHC Class II antibody and anti-ICOS antibody, or antibody fragments thereof. In some embodiments, the Tph cells are immunodetected using anti-PD-1 antibody, anti-MHC Class II antibody and anti-CCR2 antibody, or antibody fragments thereof. In some embodiments, the Tph cells are immunodetected using anti-PD-1 antibody, anti-MHC Class II antibody and anti-CCR5 antibody, or antibody fragments thereof. In some embodiments, the Tph cells are immunodetected using anti-PD-1 antibody, anti-MHC Class II antibody and anti-CX3CR1 antibody, or antibody fragments thereof. In some embodiments, the Tph cells are immunodetected using anti-PD-1 antibody, anti-ICOS antibody and anti-CCR2 antibody, or antibody fragments thereof. In some embodiments, the Tph cells are immunodetected using anti-PD-1 antibody, anti-ICOS antibody and anti-CCR5 antibody, or antibody fragments thereof. In some embodiments, the Tph cells are immunodetected using anti-PD-1 antibody, anti-ICOS antibody and anti-CX3CR1 antibody, or antibody fragments thereof.

In some embodiments, the Tph cells are immunodetected based on low or no expression of CXCR5.

In some embodiments, the method further comprises measuring Tph cell activity. In some embodiments, the Tph cell activity is B cell helper activity. In some embodiments, the Tph cell activity is measured using a co-culture of Tph cells and memory B cells. In some embodiments, the Tph cell activity is measured as autoantibody production or plasmablast differentiation.

Another aspect provides a kit comprising a PD-1 binding partner, such as an antibody or an antibody fragment specific for PD-1, a binding partner for at least one of CCR2, CCR5 and CX3CR1, such as an antibody or an antibody fragment specific for at least one of CCR2, CCR5, and CX3CR1, and binding partner for at least one of MHC Class II, ICOS, and CXCR5, such as an antibody or an antibody fragment specific for at least one of MHC Class II, ICOS, and CXCR5.

In some embodiments, the binding partners are antibodies or antibody fragments. In some embodiments, one or more of the binding partners such as antibodies or antibody fragments are fluorescently labeled.

In some embodiments, the kit further comprises one or more secondary antibodies. In some embodiments, the secondary antibodies are fluorescently labeled.

Other aspects provide a Tph cell or a Tph cell population, optionally in an isolated form. The Tph cell may be characterized according to any of the phenotypic or functional characteristics provided herein. As an example, the Tph cell(s) may be PD-1+/CXCR5−/MHC class II+ and/or PD-1+/CXCR5−/ICOS+, and additionally positive for CCR2, CCR5 and/or CX3CR1.

In the case of a Tph cell population, such population may comprise at least 25% cells characterized as PD-1+/CXCR5−/MHC class II+ and/or PD-1+/CXCR5−/ICOS+, and additionally positive for CCR2, CCR5 and/or CX3CR1. In some embodiments, the Tph cell population may comprise at least 30%, at least 35%, at least 40%, at least 45%, at least 50%, at least 60%, at least 70%, at least 80%, at least 90%, or more Tph cells.

In some embodiments, the Tph cell or Tph cell population, optionally in isolated form, may be provided in a cryopreserved form. In some embodiments, the Tph cell or Tph cell population, optionally in isolated form, may be provided attached to a solid support.

Another aspect provides a cellular lysate obtained from any of the foregoing Tph cells or Tph cell populations, optionally wherein such cells are provided in isolated form.

It should be appreciated that all combinations of the foregoing concepts and additional concepts discussed in greater detail below (provided such concepts are not mutually inconsistent) are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF DRAWINGS

It is to be understood that the Figures are not necessarily to scale, emphasis instead being placed upon generally illustrating the various concepts discussed herein.

FIGS. 1A-1G show PD-1$^{hi}$ CD4$^+$ T cells expanded in seropositive rheumatoid arthritis joints. FIG. 1A shows representative viSNE plots of mass cytometry data on gated CD4$^+$ T cells from seropositive RA synovial tissue. Each dot represents a cell. Color scale indicates level of expression of the labeled marker. Dotted circles indicate the region containing PD-1$^{hi}$ T cells. FIG. 1B shows the proportion of CD4+ T cells that express high PD-1 in synovial tissue by mass cytometry (n=6). FIG. 1C shows viSNE representation of flow cytometry data from a paired RA synovial fluid and blood sample as in FIG. 1A. FIG. 1D shows flow cytometry detection of PD-1 on CD4+ T cells from synovial fluid. FIG. 1E shows quantification PD-1$^{hi}$ cells in synovial fluid from seropositive RA (n=8) and seronegative inflammatory arthritides (n=19; seronegative RA=2, juvenile idiopathic arthritis=9, spondyloarthropathy=8). FIG. 1F shows identification of PD-1 and CXCR5 in synovial tissue by flow cytometry. FIG. 1G shows the proportion of memory CD4+ T cells that express high PD-1 and CXCR5 in seropositive RA synovial (n=6). In FIGS. 1B, 1E, and 1G a mean of ±SD is shown. *p<0.05, ***p<0.0001 Mann-Whitney test.

FIGS. 2A-2E show PD-1$^{hi}$ CXCR5$^−$ CD4$^+$ T cells expanded in circulation of patients with active, seropositive RA and decrease with response to therapy. FIG. 2A shows a flow cytometry dot plot of PD-1 and CXCR5 staining on gated memory CD4$^+$ T cells from blood. FIG. 2B shows the frequency of PD-1$^{hi}$ CXCR5$^−$ cells within circulating memory CD4$^+$ T cells in patients with seropositive RA (RA Ab$^+$, n=42), seronegative RA (RA Ab$^−$, n=16), spondyloarthropathies (SpA, n=11), and non-inflammatory control patients (control, n=35). FIG. 2C shows the frequency of PD-1$^{hi}$ subpopulations that co-express MHCII or ICOS as in FIG. 2B. FIG. 2D shows the frequency of PD-1$^{hi}$ populations in seropositive RA patients with low (n=14) or moderate-high (n=28) disease activity. FIG. 2E shows PD-1$^{hi}$ cell frequencies before and after adding an RA medication (n=13 patients; methotrexate=5, anti-TNF=3, abatacept=2, tocilizumab=2, tofacitinib=1). Median±interquartile range shown. *p<0.05, p<0.01, *p<0.001 by Kruskal-Wallis (FIGS. 2B and 2D), Mann-Whitney test (FIG. 2C), Wilcoxon test (FIG. 2E).

FIGS. 3A-3D show PD-1$^{hi}$ CXCR5$^−$ CD4$^+$ T cell expression of factors associated with B cell help. FIGS. 3A-3B show RT-PCR for cytokines (n=7 donors in FIG. 3A) and intracellular regulators (n=5 donors in FIG. 3B) in memory CD4$^+$ T cell populations from RA synovial fluid. Median±interquartile range. FIG. 3C shows cytokine and transcription factor mRNA expression in circulating PD-1$^{hi}$ CD4$^+$ T cell populations divided according to CXCR3 and CXCR5 expression, relative to PD-1$^−$ CD4$^+$ T cells (n=4 donors). Mean±SD shown. FIG. 3D shows ELISAs for CXCL13 (n=4 donors) and IL-2 (representative data from 1 of 2 donors) from sorted memory CD4+ T cell populations stimulated with anti-CD3/CD28 beads. *p<0.05, p<0.01, *p<0.001 Friedman's test compared to PD-1$^−$ MHCII$^−$ (FIGS. 3A-3B), Mann-Whitney test (FIG. 3D).

FIGS. 4A-4H show high dimensional analyses of PD-1$^{hi}$ CXCR5$^−$ and PD-1$^{hi}$ CXCR5$^+$ cells identify shared and distinct features. FIG. 4A shows viSNE plots of mass cytometry data from a representative RA patient. A circle marks the same area on each plot for reference. FIG. 4B shows proteins with significantly altered median expression in both PD-1$^{hi}$ CXCR5− and PD-1$^{hi}$ CXCR5+ cells compared to PD-1− CXCR5− memory CD4+ T cells by mass cytometry. Difference in inverse hyperbolic arcsin transformed-median expression between labeled cell population and PD-1$^-$ CXCR5$^-$ memory CD4$^+$ T cells (n=14 donors). FIG. 4C shows median mass cytometry intensity of selected markers (n=14 donors). FIG. 4D shows PCA of RNAseq transcriptomes with 581 genes selected by significant (5% FDR) ANOVA F statistic across the 8 populations. Each dot represents a cell population (n=4 donors). FIGS. 4E-4F show heatmaps of row-normalized expression of Tfh-associated genes (FIG. 4E) or chemokine receptors (FIG. 4F) in mean PD-1$^{hi}$ CXCR5$^-$ cell and PD-1$^{hi}$ CXCR5$^+$ cell RNAseq transcriptomes (PD-1$^-$ CXCR5$^-$ n=4, PD-1$^+$ CXCR5$^-$ n=15, PD-1$^-$ CXCR5$^+$ n=4, PD-1$^+$ CXCR5$^+$ n=7). FIGS. 4G-4H show flow cytometric quantification of chemokine receptor expression on blood PD-1$^{hi}$ CXCR5$^-$ and PD-1$^{hi}$ CXCR5$^+$ cells (FIG. 4G) or on PD-1$^{hi}$ CXCR5$^-$ cells in seropositive RA synovial fluid or tissue (FIG. 4H). In FIGS. 4C and 4G a mean of ±SD is shown. *p<0.01, p<0.001, *p<0.0001 Wilcoxon test.

FIG. 5A shows flow cytometry plots of circulating PD-1$^{hi}$ CD4$^+$ cell populations before (left) and after (right) 7-day in vitro stimulation with anti-CD3/CD28 beads. FIG. 5B shows quantification of CXCR5 and CCR2 expression on PD-1$^{hi}$ cell populations after in vitro stimulation (pooled data from 4 experiments using 3 different donors). **p<0.001 student's t-test. FIG. 5C shows the ratio of Bcl6/Blimp1 expression by RT-PCR in sorted PD-1$^{hi}$ cell populations with the indicated transitions in surface phenotype after in vitro stimulation. Mean±SD shown (pooled data from 3 experiments using 3 different donors). One-way ANOVA *p<0.05, p<0.01, *p<0.001.

FIGS. 6A-6I show PD-1$^{hi}$ CXCR5$^-$ cells promote antibody-secreting cell differentiation via IL-21 and SLAMF5 interactions. FIG. 6A shows flow cytometry plots and frequency of plasmablasts and plasma cells among memory B cells after co-culture with indicated circulating memory CD4$^+$ T cell populations. Data from 6 independent experiments with different donors. FIG. 6B shows the total IgG in supernatants by ELISA in co-cultures as in FIG. 6A. FIG. 6C shows co-cultures of synovial fluid memory CD4$^+$ T cell subpopulations with allogeneic B cells as in FIG. 6A. FIG. 6D shows co-cultures as in FIG. 6A with IL-21R-Ig fusion protein or IgG control. FIG. 6E shows SLAMF5 expression on memory CD4$^+$ T cells (n=10 donors). FIG. 6F shows co-cultures as in FIG. 6A with anti-SLAMF5/SLAMF6 antibody or IgG control. For FIGS. 6C, 6D, and 6F, 1 of 3 experiments with different donors showed similar results. FIG. 6G shows plasmablast frequency in RA patients as in FIGS. 1E, 1H, and 1I. Immunofluorescence microscopy for PD-1 and CD4 (FIG. 6H) or CD19 (FIG. 6I) in seropositive RA synovial tissue. In FIGS. 6A-6F a mean of ±SD is shown. *p<0.05, p<0.01, *p<0.001 Wilcoxon (FIG. 6G), Kruskal-Wallis compared to PD1$^-$ CXCR5$^-$ (FIGS. 6A, 6B, and 6E), or PD-1$^-$ (FIG. 6C), or Mann-Whitney (FIG. 6D).

FIGS. 7A-7D show the detection of PD-1$^{hi}$ CD4+ T cells in rheumatoid arthritis synovial tissue and fluid by mass and flow cytometry. FIG. 7A shows viSNE plots of mass cytometry data on gated CD4+ T cells as in FIG. 1A from two additional seropositive RA synovial tissue samples. FIG. 7B shows the gating strategy used to identify synovial tissue PD-1$^{hi}$ CD4+ T cell populations by mass cytometry. FIG. 7C shows the gating strategy used to identify synovial fluid PD-1$^{hi}$ CD4+ T cells by flow cytometry. FIG. 7D shows the detection of CXCR5 on non-T cells in disaggregated synovial tissues by flow cytometry, gated on lymphocytes by FSC/SSC.

FIG. 8A shows the frequency of PD-1$^{hi}$ CXCR5+ cells within circulating memory CD4+ T cells in patients with seropositive RA (RA Ab+, n=42), seronegative RA (RA Ab−, n=16), spondyloarthropathies (SpA, n=11), and non-inflammatory control patients (control, n=35) as in FIG. 2B. FIG. 8B shows the frequency of PD-1+ CXCR5+ cells, including intermediate or high PD-1 expression, in patients with seropositive RA (n=42) and non-inflammatory control patients (n=35). Median±interquartile range shown, with Kruskal-Wallis (FIG. 8A), Mann-Whitney (FIG. 8B) tests.

FIGS. 9A-9D show the expression of B cell helper-associated genes in circulating PD-1$^{hi}$ CD4+ T cells. FIGS. 9A-9B show mRNA expression levels of cytokines/chemokines (FIG. 9A, n=10 donors) or transcription factors/signaling molecules (FIG. 9B, n=4-5 donors) detected by RT-PCR in sorted circulating memory CD4+ T cell populations, normalized to RPL13A. *p<0.05, p<0.01, *p<0.001 Friedman's test, compared to PD-1− MHCII− group. FIG. 9C shows flow cytometric quantification of MHCII expression on circulating memory CD4+ T cell populations defined by PD-1 and CXCR5. Mean+/−SD shown. FIG. 9D shows CXCR5 and PD-1 mRNA expression by RT-PCR in indicated sorted memory CD4+ T cell populations from blood (n=2 donors).

FIGS. 10A-10C show the identification of circulating PD-1$^{hi}$ CXCR5− and PD-1$^{hi}$ CXCR5+ in mass cytometry and RNAseq analyses. FIG. 10A shows an example of gating of circulating PD-1$^{hi}$ memory CD4+ T cells in mass cytometry analyses. FIG. 10B shows the sorting strategy for isolating PD-1$^{hi}$ CXCR5− and PD-1$^{hi}$ CXCR5+ cell populations for RNA-sequencing. FIG. 10C shows hierarchical clustering of T cell subsets sorted as in FIG. 10B, with clustering based on expression of Tfh-associated genes measured in RNAseq transcriptomes.

FIGS. 11A-11C show SLAM family members and IL-21 mediate B cell-helper function of PD-1$^{hi}$ CD4+ T cells. FIG. 11A shows flow cytometric quantification of SLAM and SLAMF6 expression on memory CD4+ T cells (n=10 donors). FIG. 11B shows quantification of proportion of memory B cells with plasma cell markers after co-culture with PD-1$^{hi}$ CXCR5+ CD4+ T cells. FIG. 11C shows IgG quantification by ELISA in co-cultures of memory B cells with PD-1$^{hi}$ CXCR5− or PD-1$^{hi}$ CXCR5+ CD4+ T cells with addition of blocking antibodies against SLAMF5 and/or SLAMF6. One of 3 experiments showed similar results.

DETAILED DESCRIPTION

Figure 5C:
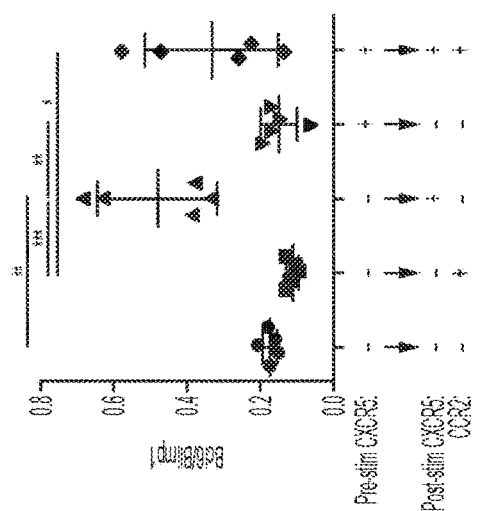
FIGS. 5A-5C show limited interconversion of PD-1$^{hi}$ CXCR5$^-$ and PD-1$^{hi}$ CXCR5$^+$ T cells.

Provided herein is a newly defined population of helper (CD4+) T cells involved in B cell maturation into antibody-secreting plasma cells. These cells, termed Tph cells herein, have now been implicated in the production of pathologic autoantibodies in certain autoimmune diseases, in accordance with this disclosure. The functional role of such Tph cells and their significance in autoimmune disease progression has not been heretofore recognized. Based on the findings described herein, methods are provided for targeting such cells in order to reduce their frequency or eliminate them entirely, in subjects having or at risk of having an autoimmune disease. Additional methods are provided for monitoring such cells, and optionally measuring their frequency, in subjects having or at risk of having an autoimmune disease, and in subjects undergoing, about to undergo, or having undergone an autoimmune therapy. These latter methods are based on the surprising association between reduction in disease activity and reduction in Tph cell frequency in RA subjects that received an autoimmune therapy. Still other methods are provided that relate to screening methods for identifying and/or designing agents that selectively, including specifically, target Tph cells, and/or down-regulate the B cell helper activity of Tph cells, and optionally selectively or specifically kill Tph cells, and methods for assessing the ability of new or existing therapies to target Tph cells, down-regulate the B cell helper activity of Tph cells, and/or kill Tph cells.

Tph Cells

Tph cells were identified by high expression of PD-1 (as compared to other T cells found in blood and synovial fluid that do not show the same potent B cell helper characteristic as Tph cells) and expression of MHC class II (MHCII) and/or ICOS, and the expression of chemokine receptors CCR2, CCR5, and CX3CR1. The cells were further found to have low or no expression of CXCR5. The absence of CXCR5 and the higher expression of chemokine receptors CCR2, CCR5, and CX3CR1 are features that distinguish Tph cells from previously described 'follicular helper' T cells (Tfh cells). The chemokine receptors CCR2, CCR5, and CX3CR1 are believed to confer migration to peripheral tissues and thus they may be responsible for the presence of Tph cells in peripheral tissues such as the synovium. Tph cells have also been characterized as CXCL13 positive (CXCL13+) and TIGIT positive (TIGIT+). This disclosure contemplates that Tph cells play an important role in driving pathologic B cell responses, including for example in the production of autoantibodies, in autoantibody-associated autoimmune diseases as well as other autoantibody-associated conditions.

Tph cells may be referred to herein as CD4+/PD-1hi/CXCR5− T cells, PD-1+/CXCR5−/MHC class II+ T cells, PD-1+/CXCR5−/ICOS+ T cells, PD-1+/CCR2+ T cells, PD-1+/CCR5+ T cells, and PD-1+/CX3CR1+ T cells.

As described in the Examples, these cells were found to be expanded in the circulation and synovial fluid of patients with seropositive RA. Specifically, the frequency of Tph cells is ~2 fold increased in the circulation of patients with seropositive RA compared to non-inflammatory control patients. Tph cells are strikingly expanded in synovial fluid from seropositive RA patients, constituting ~25% of synovial fluid CD4+ T cells.

In vitro, Tph cells induce differentiation of co-cultured memory B cells into plasmablasts upon stimulation and augment B cell antibody production. Tph cells obtained directly ex vivo from blood or synovial fluid express high levels of IL-21 and CXCL13 mRNA, with the highest levels found in MHCII+ Tph cells.

One aspect of this disclosure therefore provides an isolated Tph cell, characterized according to any of the foregoing features including without limitation as PD-1+/CXCR5− and/or PD-1+/CXCR5−/MHC class II+ and/or PD-1+/CXCR5−/ICOS+ and/or PD-1+/CCR2+ and/or PD-1+/CCR5+ and/or PD-1+/CX3CR1+.

Another aspect of this disclosure provides an isolated Tph cell population comprising at least 50% cells characterized as PD-1+/CXCR5−/MHC class II+ and/or PD-1+/CXCR5−/ICOS+. The Tph cell population may comprise at least 60%, at least 70%, at least 80%, at least 90%, at least 95%, at least 99%, or 100% cells characterized as PD-1+/CXCR5−/MHC class II+ and/or PD-1+/CXCR5−/ICOS+. Such Tph cell population may be isolated from a source or it may be produced in vitro in a proliferation assay optionally followed by a selection of Tph cells (e.g., a cell sorting process or an affinity separation process).

Such Tph cells or Tph cell populations may be provided in a cryopreserved form, including for example in solution with a cryopreservative. They may be provided in a fixative. Alternatively, they may be provided in culture together with one or more cytokines, and optionally serum or serum replacement. In still other aspects, the Tph cells may be provided in a co-culture with B cells such as memory B cells, together with culture medium suitable for maintenance of both cell types and differentiation of the co-cultured memory B cells.

In still other aspects, the Tph cells or Tph cell populations may be provided attached to or embedded in a solid or semi-solid support, such as may be used in a screening assay. The solid support may be a column or a plate. In still other aspects, the Tph cells may be used in in vitro functional assays (e.g., for antigen discovery, cytokine screens, etc.), gene expression or transcriptomic analyses, or may be used in vivo in animal models such as humanized mouse models.

In all of the foregoing aspects, the Tph cells and Tph cell populations may have been isolated from a naturally occurring source or they may have been generated in vitro.

In still further aspects, cellular lysates made from such isolated Tph cells or isolated Tph cell populations are also provided. Methods for preparing lysates from cells or cell populations are known in the art.

Treatment by Depleting or Inactivating Tph Cells

This disclosure contemplates that deletion, reduction or inactivation of Tph cells will be an effective therapy in autoimmune disease. Such a treatment is expected to markedly reduce autoantibody production that is pathogenic in autoimmune diseases. In view of the newly discovered role of Tph cells in plasmablast differentiation and autoantibody production, the disclosure further contemplates that deletion, reduction or inactivation of Tph cells will be an effective therapy in autoantibody-associated conditions including autoantibody-associated autoimmune conditions.

Such treatment aims to reduce the number and/or frequency of Tph cells and thus be more selective than current treatments. For example, rather than globally depleting B cells (as may occur upon treatment with rituximab) or globally inhibiting T cell activation (as may occur upon treatment with abatacept), the treatment methods proposed herein would selectively reduce the abnormally expanded T helper cell (Tph) population closely linked with autoantibody production in involved tissues.

The therapeutic methods described herein use agents that target Tph cells selectively or specifically. As used herein, selective targeting means that the agents preferentially target Tph cells as compared to other cells. Such agents might target other cells also but to a lesser extent. As used herein, specific targeting means that the agents target only Tph cells and no other cells. Some methods provided herein aim to selectively target Tph cells, while other aims to specifically target Tph cells. Selective targeting may be achieved, in some instances, by for example using an agent that binds to PD-1, with the expectation that more agent will bind to Tph cells, which express higher levels of PD-1, than to other cells, which express lower levels of PD-1. Agents that bind to PD-1 will be more likely to bind to Tph cells, in view of the increased frequency and high PD-1 expression of these cells, as compared to other cells.

Thus, one method provided herein comprises treating a subject having or at risk of having an autoimmune disease or an autoantibody-associated condition that is autoimmune or non-autoimmune in nature by administering a therapeutically effective amount of a Tph cell depleting or inactivating agent, wherein the Tph cell depleting or inactivating agent specifically reduces Tph cells (e.g., as may be determined by assaying the number of T cells having a Tph phenotype, including for example PD-1+ MHC class II+ CXCR5− T cells and/or PD-1+ ICOS+ CXCR5− T cells). The method may be used to treat subjects having or is at risk of developing seropositive RA or SLE, based on the surprising discovery that Tph cells are markedly expanded in seropositive RA patients and SLE patients.

Tph cell depleting agents include but are not limited to bispecific antibodies or bispecific antibody fragments, bispecific aptamers, bispecific fusion or chimeric proteins, and the like, wherein such bispecific agents bind to two cell surface markers expressed by Tph cells. For example, bispecific agents may bind to PD-1 and one of the other Tph surface markers (e.g., proteins) described herein. As another example, the bispecific fusion proteins may comprise a PD-1 ligand such as PDL-1 or PDL-2 conjugated with an antibody specific for another Tph surface protein such as those described herein. In some particular embodiments, the bispecific agents are specific for at least one of CCR2, CCR5 and CX3CR1, and may be optionally specific for PD-1.

The disclosure further contemplates localized delivery of Tph cell depleting agents. As an example, Tph cell depleting agents may be delivered to the synovium of an RA subject, including in biodegradable matrix such as a hydrogel.

The therapeutically effective amount may be an amount that results in reduction of Tph cells in the circulation or an affected tissue in the subject. In the case of RA, the Tph cells may be those in the circulation and/or the synovial fluid. Such reduction may be at least 5%, at least 10%, at least 20%, at least 30%, at least 40%, at least 50%, at least 60%, at least 70%, at least 80%, at least 90%, at least 95%, or higher percentage of the number of Tph cells prior to treatment. It will be understood in here and elsewhere in this disclosure that reduction in Tph cells may be a reduction in the absolute number of Tph cells or a reduction in the frequency of Tph cells. Provided the treatment does not affect other cell types, the reductions in absolute number and frequency should be similar. The amount required to achieve a desired level of Tph cells may be determined during clinical trials and such amount may then be used in subjects without having to assess a priori an effective amount specific for each subject. In some instances, however, it may be desirable to assess and establish a therapeutically effective amount that is individual to each subject.

Another method provided herein comprises treating a subject having or at risk of developing seropositive rheumatoid arthritis by administering a Tph cell depleting or inactivating agent to a subject characterized as having an elevated level of circulating or synovial Tph cells, such level being elevated compared to normal controls (e.g., subjects having no RA symptoms and no prior diagnosis of RA). Thus, the method may comprise first identifying a subject as one having an elevated level of circulating or synovial Tph cells (e.g., by measuring PD-1+ MHC class II+ CXCR5− and/or PD-1+ ICOS+ CXCR5− T cell numbers and comparing to such T cell numbers in normal controls), and then treating such identified subject by administering a Tph cell depleting or inactivating agent.

Tph Cell Depleting or Inactivating Agents

In some instances, a Tph cell depleting or inactivating agent comprises a targeting agent. The targeting agent may be conjugated to a cytotoxic agent, thereby generating a Tph cell depleting agent. The targeting agent is an agent that binds to Tph cells, selectively or specifically.

The targeting agent may be a PD-1 binding agent. PD-1 binding agents are known in the art. PD-1 binding agents may bind to PD-1 without impacting PD-1 function including PD-1 signaling. Thus, in some embodiments, the PD-1 binding agent is biologically inert, intending that it binds to PD-1 without stimulating or inhibiting PD-1 function. In other embodiments, the PD-1 binding agent may have agonist or antagonist activity towards PD-1. In these latter embodiments, the PD-1 binding agent may inhibit PD-1 signaling. Such agents may be used to generate a Tph cell inactivating (or inhibitory) agent.

The disclosure contemplates that in some instances the Tph depleting agent is identified by its ability to bind to cells that express high levels of PD-1 and not bind to cells that express intermediate levels of PD-1. Agents may be screened for this differential activity in vitro using cell populations known to express high levels of PD-1 and cell populations known to express lower including intermediate levels of PD-1. A population or enriched or purified Tph cells may be used as the high expressing population. T cells that are not Tph cells and thus lack the robust B cell helper activity of Tph cells have been reported to express intermediate levels of PD-1. These latter T cells are typically found in the circulation of normal or healthy subjects.

Certain targeting agents have dual binding activity, intending that they are able to bind to two markers on the surface of Tph cells. Such agents may be referred to as "bispecific" based on their ability to bind to two markers. Such agents may or may not be antibodies or antigen-binding antibody fragments thereof.

Bispecific antibodies refer to antibodies in which the two antigen-binding sites are specific for different, separate antigenic determinants. Separate antigenic determinants, in the context of this disclosure, means physically separate antigenic determinants that do not exist as part of a larger molecule. For example, separate antigenic determinants may be PD-1 and MHCII, or PD-1 and ICOS, or PD-1 and CCR5, or PD-1 and CCR2, or PD-1 and CX3CR1. Such antibodies are not naturally occurring and rather are produced synthetically such as by chemical crosslinking, fusion of hybridoma cells, or by molecular genetic approaches. As will be discussed in greater detail herein, these and other targeting agents may be used in the context of this disclosure to deliver cytotoxic agents such as drugs, toxins, radiolabeled haptens and effector cells to the Tph cells.

An example of a bispecific antibody fragment is a bispecific diabody, as described by Holliger et al. "Diabodies": small bivalent and bispecific antibody fragments. Proc Natl Acad Sci USA 1993, 90:6444-6448 and Poijak et al. Structure, 1994, 2:1121-1123. Diabodies are bivalent, bispecific antibody variants in which the VH and VL domains are expressed on a single polypeptide chain through a linker and create two antigen-binding sites. Other bispecific antibody variants include bispecific sFv molecules, as described in U.S. Pat. No. 6,699,715.

The art is familiar with methods for generating bispecific antibodies. Reference can be made, for example, to Suresh et al. Bispecific monoclonal antibodies from hybrid hybridomas. Meth. Enzymol. 1986, 121:210-228; Staerz and Bevan, PNAS 83(5):1453-1457. Bispecific antibodies may be produced using commercial entities such as Pacific Immunology, Precision Antibody, Creative Biolabs, among others. Further reference may be made to U.S. Pat. Nos. 6,060,285, 6,106,833, among others.

In some instances, the targeting agent is a bispecific fusion protein (also referred to herein as bispecific chimeric proteins). The art is familiar with methods for generating bispecific fusion proteins. Reference can be made, for example, to U.S. Pat. Nos. 6,132,992, 6,482,919, 7,115,262, 8,329,186, and 8,758,756.

Examples of bispecific targeting agents to be used in the treatment methods provided herein include an agent that binds to both PD-1 and MHCII, an agent that binds to both PD-1 and ICOS, an agent that binds to both PD-1 and CCR2, an agent that binds to both PD-1 and CCR5, and an agent that binds to both PD-1 and CX3CR1. Further examples include an agent that binds to both MHCII and ICOS, an agent that binds to both MHCII and CCR2, an agent that binds to both MHCII and CCR5, an agent that binds to both MHCII and CX3CR1. Further examples include an agent that binds to both ICOS and CCR2, an agent that binds to both ICOS and CCR5, and an agent that binds to both ICOS and CX3CR1. Further examples include an agent that binds to both CCR2 and CCR5, and an agent that binds to both CCR2 and CX3CR1. Further examples include an agent that binds to both CCR5 and CX3CR1.

Reference can also be made to published US patent application US 20120039870 which teaches methods for generating multi-specific agents such as bispecific agents.

Putative Tph cell inactivating (or inhibitory) agents may be identified or assessed based on their ability to inhibit Tph B cell helper activity as described in greater detail herein.

The Tph cell depleting agent may deplete Tph cell number by at least 10%, at least 20%, at least 30%, at least 40%, at least 50%, at least 60%, at least 70%, at least 80%, at least 90%, at least 95%, or more, including completely depleting Tph cells. The depleting activity of the agent may be assayed in vivo (e.g., in humanized mouse models) and/or in vitro.

The Tph cell inactivating (or inhibitory) agent may down-regulate Tph cell activity, including for example B cell helper activity. The agents may down-regulate such activity by at least 10%, at least 20%, at least 30%, at least 40%, at least 50%, at least 60%, at least 70%, at least 80%, at least 90%, at least 95%, or more, including completely abolishing the Tph cell activity. The depleting activity of the agent may be assayed in vivo (e.g., in humanized mouse models) and/or in vitro in for example a co-culture with memory B cells.

Cytotoxic Agents

As used herein, a cytotoxic agent is an agent that causes directly or indirectly cell death. The cytotoxic agent itself may not be selective or specific for Tph cells. However in most instances it is rendered selective or specific for Tph cells by being conjugated to a targeting agent that selectively or specifically binds to Tph cells. The cytotoxic agent may kill the Tph cell directly, meaning that it is able to kill the Tph cell without recruitment or involvement of other cell types or moieties. An example of such a cytotoxic agent is a toxin or a radioisotope.

Cytotoxic agents may be conjugated to the targeting agents described herein using for example standard chemical or recombinant DNA procedures in which the targeting agent is conjugated directly or indirectly (e.g., using a coupling agent) to the cytotoxic agent. Methods for conjugating cytotoxic agents to antibodies, for example, are known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). See for examples, the procedures described in WO 93/06231, WO 92/22583, WO 89/00195, WO 89/01476 and WO03031581. Alternatively, if the cytotoxic agent is a protein or polypeptide, conjugation may be effected using recombinant DNA procedures, including for example those described in WO 86/01533 and EP0392745.

Cytotoxic agents include, for example, antineoplastic or chemotherapeutic agents, drugs, toxins, biologically active proteins (e.g., enzymes), agonist or antagonist antibody or antibody fragments, radioisotopes.

Cytotoxic agents include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Cytotoxic agents still further include antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Cytotoxic agents also include chelated radioisotopes such as 111In and 90Y, Lu177, Bismuth213, Californium252, Iridium192 and Tungsten188/Rhenium188.

Cytotoxic agents further include drugs such as alkylphosphocholines, topoisomerase I inhibitors, taxoids and suramin.

Other cytotoxic agents include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, and the like.

Other Conjugates

This disclosure further contemplates conjugates comprising the targeting agents provided herein and detectable agents such as those used in in vivo or in vitro diagnostic applications. Examples of detectable agents include various enzymes, prosthetic groups, fluorescent materials, luminescent materials, bioluminescent materials, radioisotopes, positron emitting metals (for use in positron emission tomography), nonradioactive paramagnetic metal ions, and other heavy metals such as but not limited to those provided in Table 2. See generally U.S. Pat. No. 4,741,900 for metal ions which can be conjugated to antibodies for use as diagnostics.

Suitable enzymes include horseradish peroxidase, alkaline phosphatase, beta-galactosidase, or acetylcholinesterase; suitable prosthetic groups include streptavidin, avidin and biotin. Suitable fluorescent materials that may be used include umbelliferone, fluorescein, fluorescein isothiocyanate, rhodamine, dichlorotriazinylamine fluorescein, dansyl chloride, phycoerythrin, APC, APC-Cy7, PerCp-Cy5.5, Brilliant Violet, and the like. Suitable luminescent materials include luminol. Suitable bioluminescent materials include luciferase, luciferin, and aequorin. Suitable radioisotopes include 125I, 131I, 111In and 99Tc. In other instances, agents such as antibodies or fragments thereof may be labeled with heavy metals such as those used in mass cytometry (CyTOF). Non-limiting examples are provided in Table 2.

Secondary Agents

Various treatment methods provided herein may further comprise administration of one or more secondary agents to the subject. As used herein, a secondary agent is an agent administered to a subject in addition to the Tph cell depleting agents. The secondary agents may be those routinely administered to subjects having autoimmune disease or being at risk of developing autoimmune disease.

An example of a secondary agent that may be administered to a subject having an autoimmune disease is an anti-inflammatory agent. Examples of anti-inflammatory agents include but are not limited to non-steroidal anti-inflammatory agents such as naproxen sodium, diclofenac, sulindac, oxaprozin, diflunisal, aspirin, piroxicam, indomethicin, etodolac, ibuprofen, fenoprofen, ketoprofen, mefenamic acid, nabumetone, tolmetin sodium, and ketorolac tromethamine.

Secondary agents useful in the treatment of arthritis and other autoimmune diseases include therapeutic agents such as 5-aminosalicylic acid, .alpha.-immunokine NNSO3, ABR-215062, acetaminophen, adenosine agonists, adrenergic agents, agents that deplete or inactivate B-cells, agents that interfere with signaling by proinflammatory cytokines (such as TNFalpha) or agents which interfere with signaling by proinflammatory cytokines (such as TNFalpha) alemtuzumab, alendronate sodium, AMG-548, amitriptyline hydrochloride, anakinra, AnergiX.MS, angiotensin converting enzyme inhibitors, antegran, anti-B7 family antibody, anti-IL-6 receptor antibody, anti-IL-12, anti-IL15, anti-PD-1 family antibody, anti-TNF antibody, antibody to B-cell surface molecules, antibody to cell surface molecules (such as CD2, CD3, CD4, CD8, CD19, CD20, antibody to CD40 ligand and CD80, antiinflammatory cytokines (such as IL-4), antithrombotic agents, aspirin, aurothiomalate (intramuscular and oral), azathioprine, azathioprine sulphasalazine, CD25, CD28, CD30, CD40, CD45, CD69, CD80, CD86, CD90 (and their ligands), IL-1 (such as IRAK), balsalazide disodium, BBR-2778, beta-2 adrenoreceptor agonists (such as salbutamol), BIRB-796, budenoside, CA2 (REMICADE™), calagualine, caspase inhibitors (such as caspase-1 inhibitors), CDC-801, CDP 571, celecoxib, chemokine receptor antagonists, cholestyramine/sucrose, ciprofloxacin/dextrose-water, ciprofloxacin hydrochloride, colchicine, codeine phosphate/apap, colesevelam hydrochloride, complement inhibitors, copaxone, corticosteroids (such as prednisolone) (oral, inhaled and local injection), CPI-1189, cromoglycate, CTLA4-IG, CTLA-4-IgG, cyanocobalamin, cyanocobalamin/fa/pyridoxine, cyclophosphamide, cyclosporin, cyclosporine, D2E7, daclizumab, dexamethasone, diclofenac, diclofenac sodium, diclofenac sodium/misoprostol, diphenoxylate/atrop sulfate, dronabinol, etanercept, etodolac, fampridine, fentanyl, FK506, fluocinonide, folate, folic acid, fonotolizumab (anti-IFNg antibody), glatiramer acetate, glucosamine sulf/chondroitin, gold sodium thiomalate, hydrocodone bitartrate/apap, hydrocortisone, hydroxychloroquine sulfate, hyoscyamine sulfate, ibuprofen, IC-485, IFN-alpha-1a, IFN.alpha.1b, IKK, IL-1 (such as IRAK and TRAP), IL-1.alpha. converting enzyme inhibitors, IL-1ra, IL-2, IL-4 agonists, IL-6, IL-7, IL-8, IL-10, IL-12, IL-18 BP, IL-11, IL-13, IL-15, IL-16, IL-23, Imuran®, indomethacin, interferon gamma antagonists, infliximab, ipratropium, interferon-ala (AVONEX®); interferon-.alpha.1b (BETASERON®), interferon .alpha.-n3), interferon-a, interferon .alpha.1A-IF, ketotifen, leflunomide, levofloxacin, LEM (liposome encapsulated mitoxantrone), lidocaine hydrochloride, LJP 394 (abetimus), loperamide hydrochloride, lymphostat-B (anti-BlyS antibody), 6-MP, 6-mercaptopurines, MAP kinase inhibitors, MBP-8298, meloxicam, meperidine hydrochloride, mercaptopurine, mesalamine, mesalazine, mesopram, mesopram (PDE4 inhibitor), metalloproteinase inhibitors, methotrexate, methylprednisolone, methylprednisolone acetate, methylprednisolone sodium succinate, metronidazole, midazolam hydrochloride, mitoxantrone, MNA-715, morphine sulfate, MRA, multivitamins, mycophenolate mofetil, nabumetone, naproxen sodium, natalizumab, nedocromil, neurovax, NIK, NSAIDs, olopatadine hydrochloride misoprostol, olsalazine, olsalazine chloroquinone/hydroxychloroquine, omeprazole, oxaprozin, oxitropium, oxycodone hydrochloride, oxycodone hydrochloride/acetaminophen, p38, p55TNFRIgG (LENERCEP™), p75TNFRIgG (ENBREL®) pencillamine, phosphodiesterase inhibitors, pirfenidone allotrap 1258 (RDP-1258), piroxicam, polycarbophil, prednisone, prednisolone, promethazine hydrochloride, propoxyphene napsylate, propoxyphene napsylate/apap, rapamycin, rituximab (anti-CD20 antibody), rofecoxib, roflumilast, salmeteral, salsalate, SCIO-469, sIL-1RI, sIL-1RII, sIL-6R, sIL-6R) and antiinflammatory cytokines (such as IL-4 and TGF-beta, sinnabidol, sodium phosphate, soluble cytokine receptors and derivatives thereof (such as soluble p55 or p75 TNF), soluble cytokine receptors and derivatives thereof (such as soluble p55 or p75 TNF receptors), sTNF-R1, sulfadiazine, sulfamethoxazole/trimethoprim, sulfasalazine, sulindac, T-cell signaling inhibitors (such as kinase inhibitors), TACE inhibitors, talampanel, terbutaline, teriflunomide, tetracycline hydrochloride, TGF-beta, TGF-gamma2, THC.CBD (cannabinoid agonist), tiplimotide, thimerosal/boric acid, TNFR-Ig constructs, TR-14035, tramadol hydrochloride, triamcinolone acetonide, tyrosine kinase inhibitors, valdecoxib, VLA-4 antagonists, VLA4 Ultrahaler, VX-702, VX-740, xaliproden hydrochloride, xanthines (such as theophylline and aminophylline) and the like.

Subjects

The methods provided herein are intended for use with any subject that has or is at risk of developing an autoimmune disease or an autoantibody-associated condition such as but not limited to RA and more specifically seropositive RA. Thus, the methods are intended for human and non-human subjects including mammals including veterinary or companion animals such as dogs and cats, and agricultural animals such as horses and ponies.

Conditions

The methods and agents provided herein are contemplated for use in the treatment of autoimmune diseases. Examples of autoimmune diseases to be treated include systemic lupus erythematosus (SLE), ankylosing spondylitis, Chagas disease, chronic obstructive pulmonary disease, Crohn's Disease, dermatomyositis, diabetes mellitus type 1, endometriosis, Goodpasture's syndrome, Graves' disease, Guillain-Barre syndrome (GBS), Hashimoto's disease, hidradenitis suppurativa, Kawasaki disease, IgA nephropathy, idiopathic thrombocytopenic purpura, interstitial cystitis, mixed connective tissue disease, morphea, multiple sclerosis, myasthenia gravis, narcolepsy, neuromyotonia, pemphigus vulgaris, pernicious anaemia, psoriasis, psoriatic arthritis, polymyositis, primary biliary cirrhosis, relapsing polychondritis, rheumatoid arthritis (RA), sarcoidosis, schizophrenia, scleroderma, Sjogren's syndrome, temporal arteritis, ulcerative colitis, vasculitis, vitiligo, Wegener's granulomatosis, IgG4-related disease, anti-synthetase syndrome, and autoimmunity associated with immunodeficiency including chronic variable immunodeficiency, Wiskott-Aldrick syndrome, Good syndrome, IgA deficiency, Hyper IgM syndrome, and complement disorders. In some embodiments, the subject to has or likely to develop allograft rejection.

Some subjects may have an autoantibody-associated disease or condition. Examples of autoantibody-associated autoimmune diseases include seropositive RA, SLE, postmyocardial infarction syndrome, subacute bacterial endocarditis, anti-glomerular basement membrane nephritis, autoimmune hepatitis, primary biliary cirrhosis, alopecia areata, bullous pemphigoid, cicatricial pemphigoid, dermatitis herpetiformis, gestational pemphigoid, pemphigus vulgaris, systemic scleroderma, Addison's disease, autoimmune polyendocrine syndrome type 2, autoimmune pancreatitis, diabetes mellitus type 1, autoimmune thyroiditis, Graves' disease, Sjogren's syndrome, celiac disease, antiphospholipid syndrome, autoimmune thrombocytopenic purpura, cold agglutinin disease, pernicious anemia, thrombocytopenia, adult onset Still's disease, CREST syndrome, drug-induced lupus, enthesitis-related arthritis, juvenile arthritis, mixed connective tissue disease, palindromic rheumatism, Parry Romberg syndrome, rheumatic fever, undifferentiated connective tissue disease, dermatomysitis, myasthenia gravis, neuromyotonia, paraneoplastic cerebellar degeneration, polymyositis, Bickerstaff's encephalitis, chronic inflammatory demyelinating polyneuropathy, Guillain-Barre syndrome, Hashimoto's encephalopathy, Lambert-Eaton myasthenic syndrome, multiple sclerosis, progressive inflammatory neuropathy, Stiff person syndrome, autoimmune uveitis, neuromyelitis optica, symphathetic ophthalmia, Meniere's disease, anti-neutrophil cytoplasmic antibody-associated vasculitis, Churg-Strauss syndrome, Henoch-Schonlein purpura, microscopic polyangiitis, urticarial vasculitis, and vasculitis. Examples of autoantibody-associated autoimmune conditions include gastritis and POEMS syndrome. Examples of autoantibody-associated (non-autoimmune) diseases include agammaglobulinemia, amyotrophic lateral sclerosis, Castleman's disease, cutaneous leukocytoclastic angiitis, eczema, eosinophilic gastroenteritis, erythroblastosis fetalis, fibrodysplasia ossificans progressive, hypogammaglobulinemia, idiopathic pulmonary fibrosis, IgA nephropathy, Majeed syndrome, narcolepsy, Rasmussen's encephalitis, spondyloarthropathy, and Sweet's syndrome.

Subjects to be treated may have an autoimmune disease with evidence of Tph involvement and/or expansion. Such subjects may present with autoantibodies. Exemplary conditions include seropositive RA and SLE.

The autoimmune disease may be seropositive RA. Seropositive RA is a form of RA characterized by the presence of rheumatoid factor (RF) and anti-CCP proteins in the blood. Either protein may be detected in the blood of RA subjects in order to make a diagnosis of seropositive RA. Detection of anti-CCP is more sensitive than detection of RF, and anti-CCP may be present earlier during the progression of RA. The tests for RF and anti-CCP are routine in the art. Detection of anti-CCP and/or RF in the blood, together with one or more symptoms such as pain and swelling in the joints, involvement of many joints with inflammation, morning stiffness in the joints lasting for more than 45 minutes, imaging (e.g., X-ray) evidence of bone damage in the joints, and extra-articular (non-joint) features of RA, typically leads to a diagnosis of seropositive RA. Presence of anti-CCP and/or RF in the blood of RA subjects (i.e., seropositivity) generally indicates the subject has a more severe form of RA or is likely to develop a more severe form of RA.

Seronegative RA is defined as RA in which anti-CCP and RF are not present in the blood. This form of RA may progress differently and may respond differently to RA therapies, as compared to seropositive RA. While it has been found, in accordance with this disclosure, that seronegative RA patients did not have an expanded population of Tph cells in their synovium, it is still contemplated that such seronegative RA subjects may still derive benefit from the treatment and monitoring methods provided herein.

Also contemplated herein is treatment of autoimmune diseases characterized as having an increased frequency of Tph cells. Such an increased frequency may be regarded herein as being abnormal, intending that it differs from the frequency in a normal control.

The normal control level may be a level of Tph cells in a normal subject (i.e., a subject that does not have a condition associated with an expanded Tph cell population), or it may be the average Tph cell level in a population of normal subjects, or it may be the average Tph cell level in a random sampling of the population at large or in a random sampling of a subset of the population having the same characteristics of the subject being treated, including in the same age range, the same gender, the same medical history, etc. The control level may be one that is determined prior to the analysis of the subject rather than one that is determined in real time. The control level may therefore be a level that is obtained and established on a periodic basis (e.g., every 6 months, every year, etc.).

Detection of Tph Cells

This disclosure further provides methods for detecting and optionally measuring the number and/or frequency of Tph cells from a sample obtained from a subject. These methods may be immunodetection methods although they are not so limited. These methods may involve assaying for cells having a Tph phenotype, as described herein, and/or having a Tph activity including for example the B cell helper activity demonstrated herein for Tph cells. Thus, it will be understood that in some instances such Tph cell assays may be used to isolate and/or identify Tph cells and/or assess including measure the effect of an agent on Tph cells. If the agent is a known or putative Tph depleting agent, then the assay may measure Tph cells based on phenotype (e.g., in a FACS analysis), as an example. If the agent is a known or putative Tph inactivating (or inhibitory) agent, then the assay may measure Tph cell activity including for example B cell helper activity (e.g., in a co-culture of Tph cells and T cells such as memory B cells, with an output of plasmablast differentiation or antibody production).

Some of these methods may comprise detecting Tph cells based on their high PD-1 expression, and their expression of one, two, three, four or five markers selected from the group consisting of MHC Class II, ICOS, CCR2, CC5 and CX3CR1. The method may further comprise detecting low or no expression of CXCR5. Thus, Tph cells may be immunodetected using antibodies or antibody fragments specific for PD-1, antibodies or antibody fragments specific for MHC Class II, and antibodies or antibody fragments specific for ICOS; or antibodies or antibody fragments specific for PD-1, antibodies or antibody fragments specific for MHC Class II, and antibodies or antibody fragments specific for CCR2; or antibodies or antibody fragments specific for PD-1, antibodies or antibody fragments specific for MHC Class II, and antibodies or antibody fragments specific for CCR5; or antibodies or antibody fragments specific for PD-1, antibodies or antibody fragments specific for MHC Class II, and antibodies or antibody fragments specific for CX3CR1; or antibodies or antibody fragments specific for PD-1, antibodies or antibody fragments specific for ICOS, and antibodies or antibody fragments specific for CCR2; or antibodies or antibody fragments specific for PD-1, antibodies or antibody fragments specific for ICOS, and antibodies or antibody fragments specific for CCR5; or antibodies or antibody fragments specific for PD-1, antibodies or antibody fragments specific for ICOS, and antibodies or antibody fragments specific for CX3CR1.

Antibodies may be used to detect and measure Tph cells. Antibodies specific for any of the foregoing markers are commercially available and/or may be generated by hybridoma techniques known in the art.

Tph cells may be assayed functionally, including based on their ability to promote plasmablast differentiation in vivo and in vitro, as well as their ability to induce antibody, including autoantibody production, in vivo and in vitro. The Examples provide in vitro methods for assessing Tph cell activity in a co-culture assay with memory B cells.

As an example, memory B cells may be obtained using antibody based techniques based on the CD27$^+$ CD14$^-$ CD3$^-$ phenotype. T cell populations may be co-cultured with autologous memory B cells at a ratio of 1:10 in culture medium supplemented with serum (e.g., in 100 uL of RPMI/10% FBS) and then stimulated including for example with LPS (5 µg/mL) and SEB (1 µg/mL). The co-culture may occur for 7 days. The B cells may be autologous or allogeneic. Supernatants are collected and total IgG is measured by ELISA. Cells may be harvested and analyzed by flow cytometry, with plasmablasts defined as CD19$^+$ CD20$^{low}$ CD38$^{hi}$ CD27$^+$ and plasma cells defined as CD19$^+$ CD20$^{low}$ CD38$^{hi}$ CD27$^+$ CD138$^+$.

The sample may be a whole blood sample, or a mononuclear cell sample (e.g., a peripheral blood mononuclear cell sample), or a synovial sample of either synovial fluid or tissue, although it is not so limited. In some instances, the methods further include obtaining the sample from the subject. Detection and/or quantitation of Tph cells may be used for a number of purposes.

For example, detection and/or quantitation of Tph cells may be used to diagnose an autoimmune disease in a subject that has not been diagnosed as such. The subject may be experiencing general or specific symptoms associated with autoimmune disease.

Detection and/or quantitation of Tph cells may be used to assess the severity and/or stage of an autoimmune disease in a subject having an autoimmune disease. The presence and/or level of Tph cells may indicate or contra-indicate a treatment regimen. The subject may have rheumatoid arthritis, such as seropositive rheumatoid arthritis.

As another example, detection and/or quantitation of Tph cells may be used to identify a subject at risk of having or developing an autoimmune disease. The subject may or may not be experiencing general or specific symptoms associated with autoimmune disease.

As another example, detection and/or quantitation of Tph cells may be used to assess the efficacy of a therapy such as an anti-autoimmune disease therapy on a subject. The subject may have received the therapy, or may be receiving the therapy, or may be receiving the therapy in the immediate future (e.g., may be scheduled to receive the therapy). As described in the Examples, the level of Tph cells correlates with degree of disease activity, and thus the response to the subject to a therapy may be assessed by monitoring the level of Tph cells.

Kits

Also provided herein are kits for detecting Tph cells. Such kits may comprise binding agents to be used to detect Tph cells. Such binding agents may be antibodies or antigen-binding antibody fragments. These may be detectably labeled such as fluorescently labeled. Additionally or alternatively, the kits may further comprise secondary antibodies or antibody fragments that are themselves detectably labeled such as fluorescently labeled. The antibodies may be mono-specific antibodies or they may be bispecific antibodies.

Thus, in some instances, the kit may comprise an antibody or an antibody fragment specific for PD-1, and one or more antibodies or antibody fragments, each specific for MHC Class II, ICOS, CCR2, CCR5, CX3CR1, and CXCR5.

In still further instances, the kit may comprise culture medium, mitogens such as LPS, and other culture components that may be used in a Tph and memory B cell co-culture system to test for Tph cell activity.

Antibodies and Antibody Fragments

The term "antibodies" also encompasses different types of antibodies, e.g., polyclonal antibodies, recombinant antibodies, monoclonal antibodies, humanized antibodies or chimeric antibodies, or a mixture of these.

The antibodies may be monoclonal antibodies or polyclonal antibodies.

They may be four chain antibodies comprised of two heavy and two light chains, or they may be two chain antibodies such as those comprised of two heavy chains (such as camelid antibodies) or those comprised of a single heavy chain linked to a single light chain (such as a single chain Fvs). They can be of any type (e.g., IgG, IgE, IgM, IgD, IgA and IgY), class (e.g., IgG1, IgG2, IgG3, IgG4, IgA1 and IgA2) or subclass. As discussed below, these various antibody forms can be prepared according to conventional methodology. The antibodies and antibody fragments may be naturally occurring or non-naturally occurring including for example recombinantly produced antibodies and fragments.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

The terms Fab, Fab', Fc, Fd, pFc', F(ab')$_2$, Fv, and dAb are employed with either standard immunological meanings [Klein, *Immunology* (John Wiley, New York, N.Y., 1982); Clark, W. R. (1986) *The Experimental Foundations of Modern Immunology* (Wiley & Sons, Inc., New York); Roitt, I. (1991) *Essential Immunology*, 7th Ed., (Blackwell Scientific Publications, Oxford)]. Well-known functionally active antibody fragments include but are not limited to F(ab')$_2$, Fab, Fv and Fd fragments of antibodies. These fragments which lack the Fc fragment of intact antibody, clear more rapidly from the circulation, and may have less non-specific tissue binding than an intact antibody (Wahl et al., *J. Nucl. Med.* 24:316-325 (1983)). For example, single-chain antibodies can be constructed in accordance with the methods described in U.S. Pat. No. 4,946,778 to Ladner et al. Such single-chain antibodies include the variable regions of the light and heavy chains joined by a flexible linker moiety. Methods for obtaining a single domain antibody ("Fd") which comprises an isolated variable heavy chain single domain, also have been reported (see, for example, Ward et al., *Nature* 341:644-646 (1989), disclosing a method of screening to identify an antibody heavy chain variable region ($V_H$ single domain antibody) with sufficient affinity for its target epitope to bind thereto in isolated form). Methods for making recombinant Fv fragments based on known antibody heavy chain and light chain variable region sequences are known in the art and have been described, e.g., Moore et al., U.S. Pat. No. 4,462,334. Other references describing the use and generation of antibody fragments include e.g., Fab fragments (Tijssen, Practice and Theory of Enzyme Immunoassays (Elsevieer, Amsterdam, 1985)), Fv fragments (Hochman et al., Biochemistry 12: 1130 (1973); Sharon et al., Biochemistry 15: 1591 (1976); Ehrilch et al., U.S. Pat. No. 4,355,023) and portions of antibody molecules (Audilore-Hargreaves, U.S. Pat. No. 4,470,925). Thus, those skilled in the art may construct antibody fragments from various portions of intact antibodies without destroying the specificity of the antibodies.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication No. WO 92/04381 and published European Patent Application No. EP 0239400 teach the production and use of humanized murine antibodies in which at least a portion of the murine FR regions have been replaced by FR regions of human origin. Such antibodies, including fragments of intact antibodies with antigen-binding ability, are often referred to as "chimeric" antibodies. There are entities in the United States which will synthesize humanized antibodies from specific murine antibody regions commercially, such as Protein Design Labs (Mountain View Calif.), Abgenix, and Medarex.

Thus, in some embodiments, the antibodies are recombinant antibodies. The term "recombinant antibody", as used herein, is intended to include antibodies that are prepared, expressed, created or isolated by recombinant means, such as antibodies isolated from an animal that is transgenic for another species' immunoglobulin genes, antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences.

In yet other embodiments, the antibodies may be chimeric or humanized antibodies. As used herein, the term "chimeric antibody" refers to an antibody that combines parts of a nonhuman (e.g., mouse, rat, rabbit) antibody with parts of a human antibody. As used herein, the term "humanized antibody" refers to an antibody that retains only the antigen-binding CDRs from the parent antibody in association with human framework regions (see, Waldmann, 1991, Science 252: 1657). Such chimeric or humanized antibodies retaining binding specificity of the murine antibody are expected to have reduced immunogenicity when administered in vivo for diagnostic, prophylactic or therapeutic applications according to the disclosure.

In certain embodiments, the antibodies are human antibodies. The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo). Human antibodies are generated using transgenic mice carrying parts of the human immune system rather than the mouse system. Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals results in the production of fully human antibodies to the antigen of interest. Following immunization of these mice (e.g., XenoMouse (Abgenix), HuMAb mice (Medarex/GenPharm)), monoclonal antibodies are prepared according to standard hybridoma technology. These monoclonal antibodies have human immunoglobulin amino acid sequences and therefore will not provoke human anti-mouse antibody (HAMA) responses when administered to humans. The human antibodies, like any of the antibodies provided herein can be monoclonal antibodies.

Thus, as will be apparent to one of ordinary skill in the art, the present invention also provides for $F(ab')_2$, Fab, Fv and Fd fragments; chimeric antibodies in which the Fc and/or FR and/or CDR1 and/or CDR2 and/or light chain CDR3 regions have been replaced by homologous human or non-human sequences; chimeric $F(ab')_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes single chain antibodies.

In addition, human monoclonal antibodies may be made by any of the methods known in the art, such as those disclosed in U.S. Pat. No. 5,567,610, issued to Borrebaeck et al., U.S. Pat. No. 565,354, issued to Ostberg, U.S. Pat. No. 5,571,893, issued to Baker et al, Kozber, *J. Immunol.* 133: 3001 (1984), Brodeur, et al., *Monoclonal Antibody Production Techniques and Applications*, p. 51-63 (Marcel Dekker, Inc, new York, 1987), and Boerner et al., *J. Immunol.,* 147: 86-95 (1991). In addition to the conventional methods for preparing human monoclonal antibodies, such antibodies may also be prepared by immunizing transgenic animals that are capable of producing human antibodies (e.g., Jakobovits et al., *PNAS USA,* 90: 2551 (1993), Jakobovits et al., *Nature,* 362: 255-258 (1993), Bruggermann et al., *Year in Immunol.,* 7:33 (1993) and U.S. Pat. No. 5,569,825 issued to Lonberg).

Still other antibodies are camelid antibodies as described in PCT Publication No. WO 94/04678 and U.S. Patent Publication No. 20080124324, and their derivatives in the form of camelid nanobodies as in U.S. Pat. No. 5,759,808. Camelid antibodies and camelid nanobodies are commercially available from sources such as Ablynx (Belgium). It is to be understood that the camelid antibodies can be humanized in a manner similar to that described herein for other antibody types.

Uses of Tph Cells

This disclosure further contemplates uses of Tph cells in a variety of in vivo and in vitro methods. For example, Tph cells may be used to screen for, identify and/or compare Tph cell depleting or inactivating agents. Tph cells may be used to generate or identify agents that bind to Tph cells, including those that bind selectively or specifically to Tph cells. Tph cells may be used to identify markers expressed by Tph cells including those that are uniquely expressly by Tph cells or those preferentially expressed by Tph cells. Tph cells may also be used to identify and/or compare agents that inactivate or inhibit Tph cells including agents that down-regulate B cell helper activity of Tph cells. Tph cells may be further used to screen for agents that are agonists (i.e., agents that up-regulate the activity of Tph cells). Tph cells may be used to generate autoantibodies, thereby facilitating the analysis of such antibodies.

Effective Amounts

The Tph cell depleting or inhibitory agents are administered in effective amounts. An effective amount is a dosage of the agent sufficient to provide a medically desirable result. The effective amount may vary with the particular condition being treated, the age and physical condition of the subject being treated, the severity of the condition, the duration of the treatment, the nature of the concurrent therapy (if any), the specific route of administration and the like factors within the knowledge and expertise of the health care practitioner. The dosage may be adjusted by the individual physician in the event of any complication. Effective amounts include amounts that effect any of the changes described herein in relation to treatment. Thus an effective amount may that amount that results in a decrease in Tph cells including circulating Tph cells, as described herein, or an amount that results in reduced autoantibody level, or that amount that results in reduced symptoms associated with the condition being treated. In some instances, effective amounts may be determined using in vitro assays, and in some instances effective amounts may be determined using in vivo assays including animal models or human clinical trials.

Without limitation, effective doses may be 0.01 mg/kg per day to 1000 mg/kg per day, or from about 0.1 mg/kg to 200 mg/kg, or from about 0.2 mg/kg to about 20 mg/kg, in one or more dose administrations daily, for one or more days. Doses ranging from 1-500 mg/kg, or from 1-100 mg/kg, or from 1-50 mg/kg are contemplated. The preferred amount can be determined by one of ordinary skill in the art in accordance with standard practice for determining optimum dosage levels of the agent. It is generally preferred that a maximum dose having an acceptable safety profile according to sound medical judgment be used.

Administration Routes

A variety of administration routes are available. The methods of the invention, generally speaking, may be practiced using any mode of administration that is medically acceptable, meaning any mode that produces effective levels of the agents without causing clinically unacceptable adverse effects. The route of administration may also depend on the particular condition being treated, particularly if local administration is desired. Such modes of administration include intra-joint, oral, rectal, topical, nasal, interdermal, or parenteral routes. The term "parenteral" includes subcutaneous, intravenous, intramuscular, intraperitoneal or infusion. The route of administration may also depend in part on the nature of the agent (e.g., in some instances agents that are antibodies may be administered parenterally while agents that are small molecules may be administered orally).

The agents may be administered by any variety of regimens including chronic administration or acute administration. Non-limiting examples include more than once a day, daily, every 2, 3, 4, 5, 6 days, once a week, every 2, 3, 4 weeks, once a month, every 2, 3, 4, 5, 6, 7, 8, 9, 10, 11 months, once a year, etc.

Formulations

When used in vivo, the agents are formulated as pharmaceutical compositions or preparations. A pharmaceutical preparation is a composition suitable for administration to a subject. Such preparations are usually sterile and prepared according to GMP standards, particularly if they are to be used in human subjects. In general, a pharmaceutical composition or preparation comprises the agent(s) and a pharmaceutically-acceptable carrier, wherein the agent(s) are generally provided in effective amounts. The invention further provides a pharmaceutical composition (i.e., a pharmaceutical preparation) comprising an agent for use in the treatment of any one or more conditions discussed herein.

The term "pharmaceutically-acceptable carrier" as used herein means one or more compatible solid or liquid filler, diluents or encapsulating substances which are suitable for administration into a human or other animal. A pharmaceutically-acceptable carrier is a non-toxic material that does not interfere with the effectiveness of the biological activity of the agents of the invention. Pharmaceutically-acceptable carriers include diluents, fillers, salts, buffers, stabilizers, solubilizers and other materials which are well-known in the art. Exemplary pharmaceutically-acceptable carriers for peptides in particular are described in U.S. Pat. No. 5,211, 657. Such preparations may routinely contain salt, buffering agents, preservatives, compatible carriers, and optionally other therapeutic or prophylactic agents. When used in medicine, the salts should be pharmaceutically acceptable, but non-pharmaceutically-acceptable salts may conveniently be used to prepare pharmaceutically-acceptable salts thereof and are not excluded from the scope of the invention. Such pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compositions of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

The agents may be formulated with other therapeutic agents, such as those mentioned herein, or such agents may be formulated separately. They may be administered at the same time or at separate times. For example, the agent may be administered before, and/or with, and/or after the other therapeutic agent. Alternatively, the other therapeutic agent may be administered before, and/or with, and/or after the Tph cell depleting or inactivating agent.

Compositions suitable for parenteral administration conveniently comprise a sterile aqueous preparation of the agents, which may be isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administrations can be found in Remington's Pharmaceutical Sciences, Mack Publishing Co., Easton, Pa.

The pharmaceutical compositions may conveniently be presented in unit dosage form and may be prepared by any of the methods well-known in the art of pharmacy. All methods include the step of bringing the agent into association with a carrier which constitutes one or more accessory ingredients. In general, the compositions are prepared by uniformly and intimately bringing the agent into association with a liquid carrier, a finely divided solid carrier, or both, and then, if necessary, shaping the product. Compositions suitable for oral administration may be presented as discrete units, such as capsules, tablets, lozenges, each containing a predetermined amount of the cadherin-11 antagonist. Other compositions include suspensions in aqueous liquids or non-aqueous liquids such as a syrup, elixir or an emulsion.

The agents may be provided as a biocompatible microparticle or implant that is suitable for implantation into a subject. Exemplary bioerodible implants that are useful in accordance with this method are described in PCT International application no. PCT/US/03307 (Publication No. WO 95/24929, entitled "Polymeric Gene Delivery System", claiming priority to U.S. patent application serial no. 213, 668, filed Mar. 15, 1994). PCT/US/0307 describes a biocompatible, preferably biodegradable polymeric matrix for containing an exogenous gene under the control of an appropriate promoter. The polymeric matrix is used to achieve sustained release of the exogenous gene in the subject. The agents described herein may be encapsulated or dispersed within the biocompatible, preferably biodegradable polymeric matrix for example such as that disclosed in PCT/US/03307. The polymeric matrix preferably is in the form of a microparticle such as a microsphere (wherein, for example, the agent is dispersed throughout a solid polymeric matrix) or a microcapsule (wherein, for example, the agent is stored in the core of a polymeric shell). Other forms of the polymeric matrix for containing the agent include films, coatings, gels, hydrogels, implants, and stents. The size and composition of the polymeric matrix device is selected to result in favorable release kinetics in the tissue into which the matrix device is implanted. The size of the polymeric matrix devise is further selected according to the method of delivery which is to be used. The polymeric matrix composition can be selected to have both favorable degradation rates and also to be formed of a material which is bioadhesive. The matrix composition also can be selected not to degrade, but rather, to release by diffusion over an extended period of time.

The following Examples are included for purposes of illustration and are not intended to limit the scope of the invention.

EXAMPLES

Chronically inflamed tissues commonly accumulate plasma cells. B cells can differentiate into plasma cells within tissues and secrete autoantibodies locally in autoimmune disease. However, the helper T cell population that promotes plasma cell differentiation in non-lymphoid tissues has not been defined.

Follicular helper $CD4^+$ T (Tfh) cells, identified as $CXCR5^+$ $PD-1^+$, are prototypical B cell-helpers. However, Tfh cell localization is largely restricted to secondary lymphoid organs. We sought to identify tissue-homing B cell-helper T cells in blood and synovial fluid from patients with rheumatoid arthritis (RA), a disease characterized by synovial plasma cell accumulation and autoantibody production.

We report that $PD-1^{hi}$ $CXCR5^-$ $CD4^+$ T cells are expanded in the circulation of seropositive, but not seronegative, RA patients and are strikingly enriched in seropositive RA synovial fluid, constituting ~30% of synovial fluid $CD4^+$ T cells. Mass cytometry and transcriptomics demonstrate numerous similarities between $PD-1^{hi}$ $CXCR5^-$ T cells and $PD-1^{hi}$ $CXCR5^+$ Tfh cells, including high expression of IL-21, CXCL13, MAF, and ICOS. In vitro, both $PD-1^{hi}$ $CXCR5^-$ cells and Tfh cells induce plasmablast differentiation via IL-21 and SLAMF5-interactions. However, $PD-1^{hi}$ $CXCR5^-$ cells express a unique transcriptional signature distinct from Tfh cells that includes increased expression of Blimp1 and the inflammatory chemokine receptors CCR2, CCR5, and CX3CR1. We propose that $PD-1^{hi}$ $CXCR5^-$ $CD4^+$ T cells represent a previously undefined 'peripheral helper' T (Tph) cell population uniquely poised to support B cell responses in inflamed tissues. Given their marked expansion in seropositive RA, Tph cells may represent an important population driving pathologic autoantibody production.

Materials and Methods

Human Subjects Research

Human subjects research was performed according to the Institutional Review Board via approved protocols. Blood and synovial fluid samples were collected from patients seen at the Brigham and Women's Hospital Arthritis Center. Patients with RA fulfilled the ACR 1987 Rheumatoid Arthritis classification criteria. Rheumatoid factor and anti-CCP antibody status, C-reactive protein level, and medication usage were obtained by review of electronic medical records. CDAI was measured by the treating clinician on the day of sample acquisition. For RA patients followed longitudinally, a new treatment was initiated at the discretion of the treating physician. Blood samples were acquired before initiation of a new biologic therapy or within 1 week of starting methotrexate. Concurrent prednisone at doses <10 mg/day were permitted. Patients with any reduction in CDAI following treatment initiation were included. For all blood and synovial fluid samples, mononuclear cells were isolated by Ficoll-Hypaque (GE Healthcare Life Sciences) density centrifugation and cryopreserved for batched analyses.

Synovial Tissue Analysis

Synovial samples were acquired from discarded arthroplasty tissue. For CD4$^+$ T cell phenotyping, seropositive RA synovial tissue was isolated by careful dissection and disaggregated by enzymatic digestion with liberase TL as previously described(37). Disaggregated cells were cryopreserved for batched analyses.

Mass Cytometry

Cryopreserved disaggregated synovial cells or PBMCs were thawed into RPMI+10% FBS. Viability was assessed with rhodium for PBMCs and cisplatin (both Fluidigm) for synovial cells. Cells were then washed and stained with primary antibody cocktails at 1:100 dilution. All antibodies were obtained from the Longwood Medical Area CyTOF Antibody Resource Core (Boston, Mass.). Cells were then washed, fixed in Ebioscience Fix/Perm for 45 minutes, washed in a 0.1% saponin containing buffer, then stained for intracellular markers. Cells were re-fixed in formalin (Sigma), washed with Milli-Q water, and analyzed on a CyTOF2 for PBMC or Helios (Fluidigm) for synovial cells. Mass cytometry data were normalized using EQ™ Four Element Calibration Beads (Fluidigm) as described(38).

viSNE analyses were performed with the Barnes-Hut SNE implementation on Cytobank (see cytobank.org website) using an equal number of randomly selected cells from each sample. For synovial cell analyses, gated CD4+ T cells were analyzed using all available markers. Paired synovial fluid and blood samples were analyzed together in a single viSNE analysis for direct comparison. For comparisons of circulating PD-1$^{hi}$ CXCR5$^+$ and PD-1$^{hi}$ CXCR5$^-$, viSNE analyses were performed on gated memory CD4$^+$ T cells excluding markers used to gate these cells. Comparison of marker expression on PD-1$^{hi}$ CXCR5$^-$ and PD-1$^{hi}$ CXCR5$^+$ cells was performed with R-3.2 using permutation Wilcoxon rank-sum tests adjusted for multiple testing. Where indicated, mass cytometry data were transformed using the inverse hyperbolic sine for graphical representation (39).

Flow Cytometry and Cell Sorting

For phenotypic analyses, cryopreserved cells were thawed into warm RPMI/10% FBS, washed once in cold PBS, and stained in with antibody mixes for 45 minutes. Cells were washed in cold PBS, filtered, and data acquired on a BD FACSAria Fusion, BD Fortessa, or BD Canto II using FACSDiva software. Data were analyzed using FlowJo 10.0.7. For blood cell quantification, samples were analyzed in uniformly processed batches and a single set of gates for PD-1, CXCR5, ICOS, and MHCII was applied to all samples. For sorting of T cell populations, total CD4$^+$ T cells were isolated by magnetic bead negative selection (Miltenyi Biotec), and purified CD4$^+$ T cells were stained with primary antibody mixtures.

RT-PCR Analyses

RNA isolated using RNeasy Micro Kits (Qiagen). cDNA was prepared using Quantitect RT-PCR (Qiagen) and PCR performed with Brilliant III SYBRGreen on an a Stratagene Mx3000. Primer pairs are listed below. Expression levels relative to control gene RPL13A were calculated.

TABLE 1

RT-PCR primers

| | Forward | Reverse |
|---|---|---|
| RPL13A | CATAGGAAGCTGGGAGCAAG (SEQ ID NO. 1) | GCCCTCCAATCAGTCTTCTG (SEQ ID NO. 2) |
| TNF | CTCTTCTGCCTGCTGCACTTTG (SEQ ID NO. 3) | ATGGGCTACAGGCTTGTCACTC (SEQ ID NO. 4) |
| IL-2 | AGAACTCAAACCTCTGGAGGAAG (SEQ ID NO. 5) | GCTGTCTCAGCATATTCACAC (SEQ ID NO. 6) |
| IFN-γ | GCATCGTTTTGGGTTCTCTTG (SEQ ID NO. 7) | AGTTCCATTATCCGCTACATCTG (SEQ ID NO. 8) |
| IL-10 | CGCATGTGAACTCCCTGG (SEQ ID NO. 9) | TAGATGCCTTTCTCTTGGAGC (SEQ ID NO. 10) |
| IL-21 | AGGAAACCACCTTCCACAAA (SEQ ID NO. 11) | GAATCACATGAAGGGCATGTT (SEQ ID NO. 12) |
| CXCL13 | TCTCTGCTTCTCATGCTGCT (SEQ ID NO. 13) | TCAAGCTTGTGTAATAGACCTCCA (SEQ ID NO. 14) |
| PD-1 | CCAGGATGGTTCTTAGACTCC (SEQ ID NO. 15) | TTTAGCACGAAGCTCTCCGAT (SEQ ID NO. 16) |
| MAF | CCGTCCTCTCCCGAGTTTTT (SEQ ID NO. 17) | TGCTGGGGCTTCCAAAATGT (SEQ ID NO. 18) |
| Bcl6 | GTTTCCGGCACCTTCAGACT (SEQ ID NO. 19) | CTGGCTTTTGTGACGGAAAT (SEQ ID NO. 20) |
| BATF | TGGCAAACAGGACTCATCTG (SEQ ID NO. 21) | CTGTTTCTCCAGGTCTTCGC (SEQ ID NO. 22) |
| SAP | GCTATTTGCTGAGGGACAGC (SEQ ID NO. 23) | TGTCTGGGACACTCGGTATG (SEQ ID NO. 24) |
| Blimp1 | AACTTCTTGTGTGGTATTGTCGG (SEQ ID NO. 25) | TCTCAGTGCTCGGTTGCTTT (SEQ ID NO. 26) |

T Cell-B Cell Co-Cultures

Total B cells were isolated first from PBMCs by magnetic bead positive selection using CD19 (Miltenyi), then CD4$^+$ T cells were isolated by negative selection. B cells were stained with CD14-APC, CD3-PeCy7, and CD27-BV510 (all from Biolegend), and memory B cells sorted as CD27$^+$ CD14$^-$ CD3$^-$ cells on a BD FACSAria Fusion. Sorted T cell populations were co-cultured with autologous memory B cells at a ratio of 1:10 in 100 uL of RPMI/10% FBS and stimulated with LPS (5 µg/mL) and SEB (1 µg/mL) for 7 days. For co-cultures using synovial fluid T cells, allogeneic memory B cells from blood were used. Supernatants were collected and total IgG measured by ELISA (eBioscience). Cells were harvested and analyzed by flow cytometry, with plasmablasts defined as $CD19^+ CD20^{low} CD38^{hi} CD27^+$ and plasma cells defined as $CD19^+ CD20^{low} CD38^{hi} CD27^+ CD138^+$. For blocking experiments, 10 µg/ml anti-SLAMF5 or anti-SLAMF6 antibodies (Biolegend) or 20 µg/mL IL-21R-Ig (R&D Systems) were used.

PD-$1^{hi}$ Cell In Vitro Stimulation Assays

PD-$1^{hi}$ CXCR5− cells and PD-$1^{hi}$ CXCR5+ cells were sorted from magnetic bead-purified CD4+ T cells from blood of healthy donors and were stimulated with anti-CD3/CD28 beads for at a cell:bead ratio of 5:1 for 7 days. Cells were then re-stained with anti-PD-1 and anti-CXCR5 antibodies and $CXCR5^+$ and $CXCR5^-$ cells within each population were sorted into lysis buffer for RT-PCR analyses.

RNA Sequencing

RNA was isolated from 800-1000 cells from sorted T cell subpopulations as described. 5 uL of total RNA were placed in wells of a 96-well plate and RNA sequencing libraries were prepared at Broad Technology Labs at the Broad Institute of Harvard and MIT using the Illumina SmartSeq2 platform. Samples were sequenced on a NextSeq500 using 75 bp paired-end reads to an average depth of 9M pairs of reads per sample. All cDNA transcripts from Ensembl release 82 were quantified with Kallisto version 0.42.4(40). We used limma to model each gene as a linear combination of donor-specific effects. Next, we used the residuals from these models in ANOVA across 8 gates and selected 581 genes with significant F statistic with <5% FDR. We used these selected genes for principal components analysis. Heatmaps show relative gene expression z-scores across columns (mean 0 and variance 1). In comparisons of specific cell populations, genes with log fold change >1.2 and FDR<1% were considered differentially expressed.

Immunofluorescence Microscopy 5 micron sections of synovium frozen in OCT were fixed in 4% PFA for 10 minutes, blocked in 10% normal donkey serum in PBS for 10 minutes, and then incubated with primary antibodies (goat anti-human PD-1, mouse anti-human CD4, mouse anti-human CD19, mouse, anti-human CXCR5), followed by donkey anti-species secondaries. For detection of CXCR5, a donkey anti-mouse secondary was used followed by streptavidin-AlexaFluor 594. Sections were imaged on a microscope and images processed using Zen Black (Zeiss) and then ImageJ.

Results

Abundant PD-$1^{hi}$ CD4+ T Cells in RA Synovium

We developed a mass cytometry panel to comprehensively analyze both stromal and leukocyte populations in disaggregated synovial tissue samples (shown below). We used this panel to analyze CD4+ T cells in 3 seropositive (defined as rheumatoid factor+ or anti-citrullinated peptide antibody+) RA synovial samples with dense leukocyte infiltrates. Dimensional reduction with the viSNE algorithm (14) allowed for visualization of CD4+ T cell populations arranged in 2 dimensions based on expression of all 36 assayed proteins (FIG. 1A). Interrogating the 2-D viSNE plots for expression of 5 different activation markers (PD-1, MHCII, ICOS, CD69, CD38) revealed distinct expression patterns. CD69 was broadly expressed on infiltrating CD4+ T cells, while CD38 expression was the most restricted. Strikingly, a large population of aggregated cells was characterized by high expression of PD-1 in all three samples (FIG. 1A, FIG. 7A). Biaxial gating of data from 6 seropositive RA samples confirmed high expression of PD-1 on ~25% of synovial CD4+ T cells, the majority of which co-expressed MHCII and/or ICOS (FIG. 1B, gated as in FIG. 7B).

TABLE 2

Mass cytometry panel for analysis of synovial cells

| Target | Clone | Metal |
|---|---|---|
| CD45 | HI30 | 89Y |
| CD27 | O323 | 141Pr |
| CD19 | HIB19 | 142Nd |
| RANKL | MIH24 | 143Nd |
| CD64 | 10.1 | 144Nd |
| CD16 | 3G8 | 145Nd |
| CD8α | RPA T8 | 146Nd |
| FAP | Poly | 147Sm |
| CD20 | 2H7 | 148Nd |
| CD45RO | UCHL1 | 149Sm |
| CD38 | HIT2 | 150Nd |
| PD-1 | EH12.2H7 | 151Eu |
| CD14 | M5E2 | 152Sm |
| CD69 | FN50 | 153Eu |
| CXCR5 | J252D4 | 154Sm |
| CD4 | RPA T4 | 155Gd |
| Podoplanin | NC-08 | 156Gd |
| CD3 | UCHT1 | 158Gd |
| CD11c | Bu15 | 159Tb |
| FcRL4 | 413D12 | 160Gd |
| CD138 | MI15 | 161Dy |
| CD90 | 5E 10 | 162Dy |
| CCR2 | K036C2 | 163Dy |
| Cadherin11 | 23C6 | 164Dy |
| FoxP3 | PCH101 | 165Ho |
| CD34 | 581 | 166Er |
| CD146 | SHM-57 | 167Er |
| IgA | 9H9H11 | 168Er |
| TCRγδ | B1 | 169Tm |
| ICOS | C398.4A | 170Er |
| CD66b | G10F5 | 171Yb |
| IgM | MHM-88 | 172Yb |
| CD144 | BV9 | 173Yb |
| MHCII | L243 | 174Yb |
| IgD | IA6-2 | 175Lu |
| VCAM-1 | STA | 176Yb |
| Live/Dead | | 195Pt |

In a complementary approach, we used viSNE to visualize 11-dimensional flow cytometry analyses of memory CD4+ T cells from paired synovial fluid and blood samples from 3 established seropositive RA patients who underwent joint aspiration for diagnostic or therapeutic purposes (FIG. 1C, see below). Evaluation of 4 activation markers (PD-1, MHCII, ICOS, CD49d) similarly highlighted a large population of PD-$1^{hi}$ CD4+ T cells in seropositive RA synovial fluid. As with synovial tissue, a subset of PD-$1^{hi}$ cells co-expressed MHCII and/or ICOS. Biaxial gating of data from 8 seropositive RA patient samples confirmed high PD-1 expression on ~30% of synovial fluid CD4+ T cells, mirroring results from synovial tissue (FIGS. 1D-1E gated as in FIG. 7C).

TABLE 3

Flow cytometry panel for identifying PD-1hi cells

| Target | Clone | Fluorophore |
|---|---|---|
| CD27 | TB01 | FITC |
| CXCR3 | CEW33D | PE |
| CD4 | RPA-T4 | PE-Cy7 |
| ICOS | ISA-3 | PerCP-Cy5.5 |
| CXCR5 | J252D4 | BV421 |
| CD45RA | HI100 | BV510 |

TABLE 3-continued

Flow cytometry panel for identifying PD-1hi cells

| Target | Clone | Fluorophore |
|---|---|---|
| HLA-DR | G46-6 | BV605 |
| CD49d | 9F10 | BV711 |
| PD-1 | EH12.2H7 | APC |
| CD3 | HIT3A | AlexaFluor700 |
| CD29 | TS2/16 | APC-Cy7 |
| Live/Dead |  | Propidium iodide |

To evaluate the specificity of this observation, we compared the frequency of PD-1$^{hi}$ CD4$^+$ T cell populations in synovial fluid from patients with seropositive RA and patients with seronegative inflammatory arthritides (seronegative RA, spondyloarthropathies, juvenile idiopathic arthritis). Strikingly, PD-1$^{hi}$ cells were dramatically enriched specifically in the seropositive RA patients (p<0.0001, Mann-Whitney) (FIGS. 1D-1E).

The association of synovial PD-1$^{hi}$ CD4$^+$ T cells with seropositive RA, but not seronegative arthritides, led us to consider whether these cells might be Tfh cells, which are often identified as CXCR5$^+$ PD-1$^+$ (13). However, in seropositive RA synovial tissue, PD-1$^{hi}$ CXCR5$^-$ cells outnumbered PD-1$^{hi}$ CXCR5$^+$ cells by 8-fold (FIGS. 1F-1G). Lack of CXCR5 was not an artifact of tissue disaggregation, as CXCR5 could be readily detected on synovial CD3$^-$ leukocytes, likely B cells (FIG. 7D). In synovial fluid, fewer than 2% of CD4$^+$ T cells expressed CXCR5 in all samples tested. Thus, the vast majority of PD-1$^{hi}$ CD4$^+$ T cells in synovium are not Tfh cells.

Circulating PD-1$^{hi}$ CXCR5$^-$ T Cells in RA

Figure 8A:
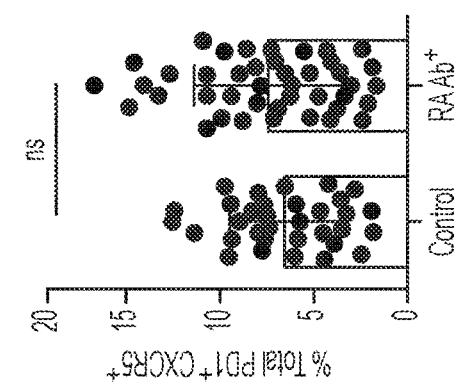
FIGS. 8A-8B show the quantification of circulating Tfh cells in seropositive RA patients.
Figure 8B:
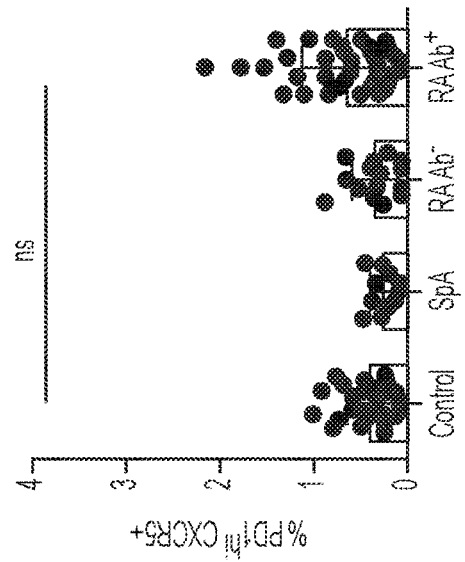

Intriguingly, PD-1$^{hi}$ CXCR5$^-$ CD4$^+$ T cells with a similar multidimensional phenotype also appeared in the circulation, albeit at much lower frequencies (FIG. 1C, FIG. 2A). Quantification of circulating PD-1$^{hi}$ CXCR5$^-$ memory CD4$^+$ T cells in a cross-sectional cohort of patients with established seropositive RA, seronegative RA, spondyloarthropathies, and non-inflammatory controls demonstrated an increased frequency of PD-1$^{hi}$ CXCR5$^-$ cells, but not PD-1$^{hi}$ CXCR5$^+$ cells, specifically in seropositive RA patients (FIG. 2B, see below, and FIGS. 8A-8B). Consistent with synovial cell phenotypes, PD-1$^{hi}$ MHCII$^+$ CXCR5$^-$ and PD-1$^{hi}$ ICOS$^+$ CXCR5$^-$ cells were also increased in the seropositive RA patients (FIG. 2C). PD-1$^{hi}$ CXCR5$^-$ cell frequencies were more robustly increased in seropositive RA patients with moderate or high disease activity (clinical disease activity index (CDAI)>10), compared to patients with low disease activity (CDAI≤10) (FIG. 2D).

TABLE 4

Clinical characteristics of patients evaluated

|  |  |  | Seronegative | |
|---|---|---|---|---|
|  | Control | Seropositive RA | RA | SpA |
| Number | 35 | 42 | 16 | 11 |
| Age | 61 ± 13 | 58 ± 14 | 58 ± 13 | 48 ± 12 |
| Female | 22 (63) | 33 (78) | 11 (69) | 5 (45) |
| Disease Duration (yrs) | N/A | 13 ± 9 | 14 ± 10 | 10 ± 6 |
| C-reactive protein (mg/L) | ND | 9.3 ± 17.4 | 6.3 ± 8.5 | 3.9 ± 4.2 |
| CDAI | ND | 13.7 ± 8.1 | 9.8 ± 7.6 | ND |
| Methotrexate | 0 | 19 (45) | 8 (50) | 2 (18) |
| Anti-TNF | 0 | 16 (38) | 6 (38) | 10 (90) |
| Other biologics | 0 | 10 (24) | 5 (31) | 0 |
| Other synthetic DMARDs | 0 | 4 (10) | 1 (6) | 0 |

Average ± SD are shown.
Parentheses indicate proportion of patients.
Other synthetic DMARDs = azathioprine, sulfasalazine, hydroxychloroquine
Other biologics include abatacept, rituximab, tocilizumab, tofacitinib.

Changes in PD-1$^{hi}$ cell frequencies are not explained by medication effects because seronegative RA patients, who were similarly treated with methotrexate (seropositive 45%, seronegative 50%) and biologic therapies (seropositive 62%, seronegative 68%), did not show increased PD-1$^{hi}$ cell frequencies. In an independent, longitudinal cohort of 13 seropositive RA patients who experienced reduced disease activity 3 months after starting a new RA medication, the frequency of PD-1$^{hi}$ CXCR5$^-$ cells, PD-1$^{hi}$ MHCII CXCR5$^-$ and PD-1$^{hi}$ ICOS$^+$ CXCR5$^-$ cells decreased significantly after treatment escalation (FIG. 2E).

PD-1$^{hi}$ Cells Express B Cell-Helper Factors

High PD-1 expression is often associated with an anergic or dysfunctional state. To assess the potential function of synovial PD-1$^{hi}$ cells, we isolated PD-1$^{hi}$ CD4+ T cells from synovial fluid and measured cytokine and regulatory factor expression by RT-PCR. Surprisingly, despite lack of CXCR5, PD-1$^{hi}$ cells expressed markedly elevated mRNA levels of IL-21 and CXCL13, and higher levels of IFN-γ and IL-10, compared to PD-1$^-$ T cells, with the highest expression in PD-1$^{hi}$ MHCII$^+$ cells (FIG. 3A). In contrast, IL-2 showed a trend towards lower expression in PD-1$^{hi}$ cells. The >100-fold increased IL-21 and >1000-fold increased CXCL13 expression in PD-1$^{hi}$ cells indicates that these cells are not globally 'exhausted,' yet the lack of elevation of IL-2 argues against high PD-1 expression simply marking all activated T cells. Rather, the high IL-21 and CXCL13 expression suggested possible B cell-helper function. Supporting this hypothesis, PD-1$^{hi}$ MHCII$^+$ cells in RA synovial fluid also expressed high levels of the transcription factors MAF and BATF and the signaling adaptor SAP (encoded by SH2D1A), 3 factors important for Tfh cell development or function (FIG. 3B)(13). However, in contrast to germinal center Tfh cells(13), Bcl6 was not elevated in synovial fluid PD-1$^{hi}$ cells, while Blimp1 (encoded by PRDM1) expression was increased.

A similar transcriptional pattern was seen in PD-1$^{hi}$ MHCII$^+$ CD4$^+$ T cells sorted ex vivo from the circulation, with increased expression of IL-21, CXCL13, and IFN-γ, but not IL-2, in circulating PD-1$^{hi}$ MHCII$^+$ cells compared to PD-1$^-$ cells (FIG. 9A). Increased expression of MAF, SAP, and Blimp1, but not Bcl6, was also observed (FIG. 9B). In circulating memory CD4$^+$ T cells, MHCII expression is 5-fold more frequent on CXCR5$^-$ cells compared to CXCR5$^+$ cells (FIG. 9C). When circulating PD-1$^{hi}$ CD4$^+$ cells were subdivided based on expression of CXCR5 and CXCR3, increased IL-21 and CXCL13 expression were seen in both CXCR5$^-$ and CXCR5$^+$ populations, compared to PD-1$^-$ T cells (FIG. 3C). Notably, Blimp1 expression was higher in PD-1$^{hi}$ CXCR5$^-$ cells than in PD-1$^{hi}$ CXCR5$^+$ cells, while Bcl6 expression was similar. As a control, CXCR5 mRNA transcripts were highly enriched in sorted CXCR5$^+$ T cells compared to CXCR5$^-$ cells (FIG. 9D). Consistent with transcript levels, stimulated PD-1$^{hi}$ memory CD4+ T cells produced more CXCL13 protein, but less IL-2, than did PD-1⁻ memory CD4⁺ T cells (FIG. 3D). Thus, PD-1$^{hi}$ CXCR5⁻ cells from joints and circulation express factors associated with B cell-helper function.

High Dimensional Analyses of PD-1$^{hi}$ Cells

To compare the phenotypes of PD-1$^{hi}$ CXCR5⁻ and PD-1$^{hi}$ CXCR5⁺ cells more broadly, we analyzed a set of 24 protein markers, including PD-1 and CXCR5, on CD4⁺ T cells from blood by mass cytometry (see below, gated as in FIG. 10A). Dimensional reduction and visualization of the mass cytometry data on memory CD4⁺ T cells from 4 RA patients and 4 non-inflammatory controls demonstrated that most PD-1$^{hi}$ cells clustered together (FIG. 4A, circle). The majority of PD-1$^{hi}$ cells were CXCR5⁻; however, a small population of PD-1$^{hi}$ CXCR5⁺ Tfh cells clustered adjacent to the PD-1$^{hi}$ CXCR5– cells, indicating a similar multidimensional cytometric phenotype (FIG. 4A). Consistent with flow cytometry results, a subset of PD-1$^{hi}$ CXCR5⁻ cells expressing MHCII clustered apart from PD-1$^{hi}$ CXCR5⁺ cells. FoxP3⁺ regulatory T cells aggregated in a separate region, indicating that most PD-1$^{hi}$ cells are not regulatory T cells.

TABLE 5

Mass cytometry panel for phenotyping blood PD-1hi cells.

| Target | Clone | Metal |
|---|---|---|
| Live/Dead | | 103Rh |
| CD27 | M-T271 | 141Pr |
| CD45RA | HI100 | 142Nd |
| CD44 | BJ18 | 143Nd |
| CD39 | A1 | 144Nd |
| CD16 | 3G8/B73.1 | 145Nd |
| CD8α | RPA T8 | 146Nd |
| CD45RO | UCHL1 | 147Sm |
| CD28 | CD28.2 | 148Nd |
| CD25 | M-A251 | 149Sm |
| PD-1 | EH12.2H7 | 151Eu |
| CD69 | FN50 | 153Eu |
| CXCR5 | J252D4 | 154Sm |
| CD4 | RPA T4 | 155Gd |
| CD73 | AD2 | 156Gd |
| CD3 | UCHT1 | 158Gd |
| CD57 | HCD57 | 159Tb |
| ICOS | C398.4A | 160Gd |
| CXCR3 | G025H7 | 162Dy |
| CD161 | HP-3G10 | 164Dy |
| FoxP3 | PCH101 | 165Ho |
| CD38 | HIT2 | 167Er |
| CCR6 | G034E3 | 168Er |
| CCR7 | G043H7 | 170Er |
| CD127 | A019D5 | 171Yb |
| CD122 | TU27 | 172Yb |
| TIGIT | MBSA43 | 173Yb |
| HLA-DR | L243 | 174Yb |
| Tbet | 4810 | 175Lu |
| Perforin | dG9 | 176Yb |

Compared to PD-1⁻ CXCR5⁻ cells, both PD-1$^{hi}$ CXCR5⁻ cells and PD-1$^{hi}$ CXCR5⁺ cells showed significantly increased expression of 11 proteins, including TIGIT, ICOS, CD38, and CD57, and significantly decreased expression of 5 proteins, including the cytokine receptors CD25 and CD127 (FIG. 4B). Despite clustering in close proximity by viSNE, PD-1$^{hi}$ CXCR5⁻ cells showed specific expression differences from PD-1$^{hi}$ CXCR5⁺ cells, such as lower expression of CCR7 and CD27 but higher CD44 and Tbet (FIGS. 4B-4C). The low expression of a CCR7, a lymph node-homing receptor(15), and higher expression of CD44, a hyaluronan receptor important for migration to inflamed tissues(16), suggest distinct migratory capacities of PD-1$^{hi}$ CXCR5⁻ cells and PD-1$^{hi}$ CXCR5⁺ cells.

Advances in library preparation have now enabled query of the transcriptome with <2000 cells, enabling an unbiased transcriptional comparison of PD-1$^{hi}$ CXCR5⁻ cells and PD-1$^{hi}$ CXCR5⁺ cells (17). Eight memory CD4+ T cell populations, including PD-1$^{hi}$ CXCR5⁻ and PD-1$^{hi}$ CXCR5⁺ cell subpopulations defined by expression of MHCII and ICOS, (gated in FIG. 10B) were sorted from blood from 4 patients with active, seropositive RA. Samples from each sorted T cell subpopulation clustered together by principal components analysis (PCA) (FIG. 4D). PD-1$^{hi}$ populations that co-expressed ICOS and/or MHCII were similarly separated from PD-1⁻ cells along the first principal component, irrespective of CXCR5 expression (PC1) (FIG. 4D). In contrast, PD-1$^{hi}$ CXCR5⁻ and PD-1$^{hi}$ CXCR5⁺ cell populations were largely distinguished by the second principal component (PC2), indicating considerable differences in the global transcriptomes of PD-1$^{hi}$ CXCR5⁻ cells and PD-1$^{hi}$ CXCR5⁺ cells beyond CXCR5 expression alone.

To identify genes with similar expression patterns in PD-1$^{hi}$ CXCR5⁻ cells and PD-1$^{hi}$ CXCR5⁺ cells, we tested global differential expression comparing all of the PD-1$^{hi}$ populations to all PD-1⁻ populations. Sixty-six genes were significantly differentially expressed (log fold change >1.2, FDR<0.01, list provided below), including a set of genes previously reported to be elevated in Tfh cells, such as MAF, TIGIT, and SLAMF6 (18, 19). Analysis of a curated list of Tfh-associated genes (18, 20, 21) demonstrated similar upregulation of multiple genes in the pooled PD-1$^{hi}$ CXCR5⁺ cell samples and PD-1$^{hi}$ CXCR5⁻ cell samples (FIG. 4E). When all 8 memory CD4⁺ T cell populations listed in FIG. 4D were analyzed without pooling, hierarchical clustering of cell populations based on this gene list perfectly segregated all PD-1$^{hi}$ populations from the PD-1⁻ populations, regardless of CXCR5 expression (p<0.026, FIG. 10C). These results highlight a shared transcriptional program associated with B cell-helper function in PD-1$^{hi}$ CXCR5⁻ cells and Tfh cells.

TABLE 6

Significantly differentially expressed genes between PD-1negative and PD-1hi cell samples

| Gene | logFC PD-1negative Vs PD-1hi | p-value | adjusted p-value |
|---|---|---|---|
| PD-1 | −6.394163674 | 1.03E−17 | 2.07E−13 |
| TOX | −3.973939225 | 7.21E−13 | 7.21E−09 |
| ITM2A | −1.206121015 | 4.54E−10 | 3.02E−06 |
| TIGIT | −1.919479399 | 1.03E−09 | 5.15E−06 |
| MAF | −1.424142776 | 4.43E−09 | 1.77E−05 |
| CA6 | 3.052456565 | 6.13E−09 | 2.04E−05 |
| CST7 | −3.162619611 | 1.47E−08 | 3.80E−05 |
| SCML1 | 3.900002703 | 1.71E−08 | 3.80E−05 |
| SCO2 | −5.202859453 | 1.67E−08 | 3.80E−05 |
| CDCA7 | −4.502988841 | 2.56E−08 | 5.12E−05 |
| RAB37 | −1.574133208 | 6.90E−08 | 0.00011507 |
| ICA1 | −2.953123584 | 2.32E−07 | 0.00032355 |
| EZH2 | −3.019907996 | 2.43E−07 | 0.00032355 |
| GZMK | −2.753052708 | 2.68E−07 | 0.0003348 |
| MAP3K9 | −2.362184122 | 4.44E−07 | 0.00052219 |
| PFN1 | −1.46238995 | 7.05E−07 | 0.0007049 |
| SLAMF6 | −1.241364005 | 8.88E−07 | 0.00081759 |
| EPSTI1 | −2.040445226 | 8.99E−07 | 0.00081759 |
| NEFL | 4.046814543 | 1.14E−06 | 0.00098964 |
| CHN1 | −3.450144917 | 1.22E−06 | 0.00100506 |
| UBE2L6 | −1.228575119 | 1.55E−06 | 0.00114463 |
| FANCI | −2.790697425 | 1.77E−06 | 0.00126421 |
| PSMA4 | −1.420908253 | 2.22E−06 | 0.00148222 |

TABLE 6-continued

Significantly differentially expressed genes between PD-1negative and PD-1hi cell samples

| Gene | logFC PD-1negative Vs PD-1hi | p-value | adjusted p-value |
|---|---|---|---|
| TOX2 | -3.637770018 | 2.72E-06 | 0.00169866 |
| FABP5 | -2.439672325 | 3.07E-06 | 0.0018062 |
| ANXA2 | -1.269580271 | 3.38E-06 | 0.00193268 |
| CTLA4 | -1.739000105 | 4.31E-06 | 0.00233078 |
| PLAG1 | 3.599551478 | 4.77E-06 | 0.00251047 |
| HVCN1 | -3.516538014 | 5.08E-06 | 0.00260528 |
| FAM210A | -2.782673649 | 5.37E-06 | 0.00268396 |
| ALOX5 | 3.436967858 | 5.88E-06 | 0.00279953 |
| RGS1 | -1.204580998 | 6.09E-06 | 0.00283456 |
| MYL6B | -3.072692168 | 8.27E-06 | 0.00365101 |
| CEP128 | -3.16366403 | 8.18E-06 | 0.00365101 |
| ENC1 | -3.605191323 | 8.40E-06 | 0.00365101 |
| MIS18BP1 | -2.065611325 | 8.89E-06 | 0.00378448 |
| F5 | -1.463762553 | 1.00E-05 | 0.0040495 |
| FN1 | 2.504688725 | 1.07E-05 | 0.0040495 |
| CXCR3 | -3.01503276 | 1.06E-05 | 0.0040495 |
| ASB13 | 3.35115795 | 1.06E-05 | 0.0040495 |
| HIST2H2BF | 3.678067821 | 9.85E-06 | 0.0040495 |
| PRR5L | -2.171927479 | 1.10E-05 | 0.00407801 |
| KRT72 | 3.194468773 | 1.24E-05 | 0.00442771 |
| BZRAP1 | -1.970565679 | 1.37E-05 | 0.00480775 |
| DUSP2 | -1.459107208 | 1.55E-05 | 0.00533004 |
| DHFR | -2.732987087 | 1.74E-05 | 0.0056215 |
| FBXO41 | -2.405412912 | 1.94E-05 | 0.00614422 |
| CCDC86 | -3.430212114 | 1.99E-05 | 0.00620599 |
| FCRL3 | -1.770956334 | 2.06E-05 | 0.00627086 |
| AKR1C3 | -3.308816301 | 2.07E-05 | 0.00627086 |
| SHMT2 | -1.534205662 | 2.17E-05 | 0.00637599 |
| DDX54 | -1.733666484 | 2.21E-05 | 0.00641126 |
| UBE2A | -1.316870902 | 2.88E-05 | 0.00768207 |
| ANXA9 | 2.915422557 | 2.85E-05 | 0.00768207 |
| TUBB4B | -1.239062048 | 3.12E-05 | 0.0080967 |
| TIMELESS | -2.607726722 | 3.24E-05 | 0.00825538 |
| CCL5 | -3.355363898 | 3.26E-05 | 0.00825538 |
| UQCRC1 | -1.286406184 | 3.42E-05 | 0.00844236 |
| TBC1D4 | -1.300326318 | 3.49E-05 | 0.00851463 |
| SYT11 | -1.382472289 | 3.88E-05 | 0.00923088 |
| PMAIP1 | -2.193153793 | 3.84E-05 | 0.00923088 |
| DIRC2 | -2.784076776 | 4.00E-05 | 0.00930467 |
| SOX8 | 1.93871557 | 4.26E-05 | 0.00979931 |
| SPG20 | 1.801986978 | 4.50E-05 | 0.00989903 |
| DPP3 | -1.957767214 | 4.39E-05 | 0.00989903 |
| DUSP4 | -2.502643153 | 4.50E-05 | 0.00989903 |

We also identified 16 genes with significantly different expression between PD-1$^{hi}$ CXCR5$^-$ and PD-1$^{hi}$ CXCR5$^+$ cells, see below. Notably, PD-1$^{hi}$ CXCR5$^-$ cells showed 34-fold increased expression of CCR2, a chemokine receptor that mediates migration to sites of peripheral inflammation (22, 23). A targeted analysis of chemokine receptor expression on PD-1$^{hi}$ CXCR5$^-$ cells demonstrated striking upregulation of a set of 'inflammatory' chemokine receptors on these cells, including CCR2, CCR5, and CX3CR1 (FIG. 4F) (24). We confirmed more frequent expression of CCR2, CX3CR1, and CCR5 on circulating PD-1$^{hi}$ CXCR5- cells (FIG. 4G). Notably, ~50% of PD-1$^{hi}$ CXCR5$^-$ cells in seropositive RA synovial fluid and synovial tissue expressed CCR2 (FIG. 4H). These results indicate that while PD-1$^{hi}$ CXCR5$^-$ cells can be distinguished from Tfh cells not only by the lack of CXCR5 but also by high expression inflammatory chemokine receptors.

TABLE 7

Significantly differentially expressed genes between PD-1hi CXCR5- cell and PD-1hi CXCR5+ cell samples

| Gene | logFC PD-1hi CXCR5- vs PD-1hi CXCR5+ | p-value | adjusted p-value |
|---|---|---|---|
| RPL39 | -1.234532087 | 1.42E-07 | 0.00023032 |
| LSP1 | 1.200685645 | 2.65E-07 | 0.00029438 |
| RPL34 | -1.273114838 | 7.88E-07 | 0.00047747 |
| TTC4 | 4.631494115 | 1.29E-06 | 0.00063025 |
| LIME1 | 1.562056436 | 2.07E-06 | 0.00092044 |
| CCR2 | 5.094906534 | 2.25E-06 | 0.00095781 |
| ACTN4 | 2.323677525 | 2.83E-06 | 0.00113075 |
| CTSH | 2.649046873 | 3.19E-06 | 0.00125126 |
| PLAC8 | -1.351296215 | 6.85E-06 | 0.00236078 |
| GLIPR2 | 1.396871219 | 7.14E-06 | 0.00237986 |
| PRR5 | 2.819632034 | 1.02E-05 | 0.00305734 |
| RGS19 | 2.456286463 | 1.19E-05 | 0.00344646 |
| SAMD3 | 1.24882546 | 2.50E-05 | 0.00650593 |
| FOS | -1.595174448 | 3.68E-05 | 0.008767 |
| ANXA4 | 2.266594524 | 4.03E-05 | 0.00937053 |
| LTK | 3.888867594 | 4.20E-05 | 0.009657 |

Limited Interconversion of PD-1$^{hi}$ Cells

Figure 5B:
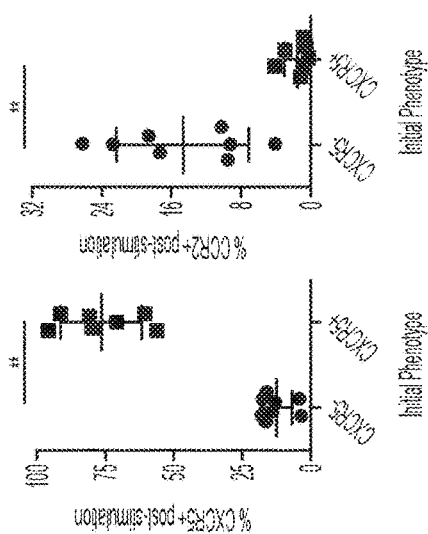
Figure 5A:
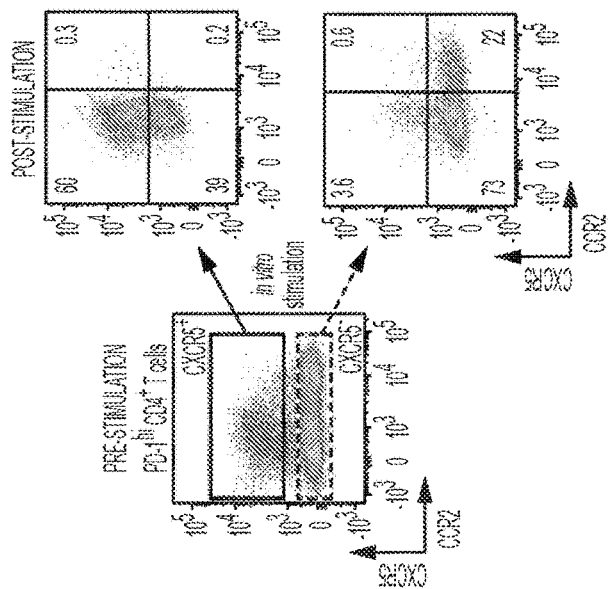

To investigate the interconversion of circulating PD-1$^{hi}$ CXCR5$^-$ and PD-1$^{hi}$ CXCR5$^+$ cells, we stimulated sorted PD-1$^{hi}$ CXCR5$^-$ and PD-1$^{hi}$ CXCR5$^+$ cell populations in vitro with anti-CD3/CD28 beads for 7 days and then re-analyzed surface phenotypes. After stimulation, ~12% of PD-1$^{hi}$ CXCR5$^-$ cells acquired CXCR5. Conversely, ~25% of PD-1$^{hi}$ CXCR5$^+$ cells lost CXCR5$^-$ expression; however, these cells did not acquire CCR2 expression (FIGS. 5A-5B). Comparing PD-1$^{hi}$ CXCR5$^+$ cells that became CXCR5$^-$ to those that remained CXCR5$^+$, we observed a decreased Bcl6/Blimp1 mRNA ratio (FIG. 5C). Conversely, in PD-1$^{hi}$ CXCR5$^-$ cells that acquired CXCR5 expression, we noted an increased Bcl6/Blimp1 ratio that was comparable to stable PD-1$^{hi}$ CXCR5$^+$ cells. Stimulated PD-1$^{hi}$ CXCR5$^-$ cells that remained CXCR5$^-$ had a low Bcl6/Blimp1 ratio. Thus, some PD-1$^{hi}$ cells may modulate CXCR5 expression upon stimulation, with concordant alterations in Bcl6 and Blimp1 expression. However, expression of the inflammatory chemokine receptor CCR2 remained restricted to the initial PD-1$^{hi}$ CXCR5$^-$ population.

PD-1$^{hi}$ CXCR5$^-$ T Cells Induce Plasma Cells

We next tested directly whether PD-1$^{hi}$ CXCR5$^-$ CD4+ T cells can provide B cell help in vitro. Both PD-1$^{hi}$ CXCR5$^-$ cells and PD-1$^{hi}$ CXCR5$^+$ cells potently induced differentiation of co-cultured memory B cells into plasma cells and enhanced IgG production (FIGS. 6A-6B). Similarly, PD-1$^{hi}$ CXCR5$^-$ CD4$^+$ T cells from synovial fluid stimulated more plasma cell differentiation than did PD-1$^-$ or PD-1$^{intermediate}$ cells (FIG. 6C). Neutralization of IL-21 with soluble IL-21R-Ig inhibited plasma cell differentiation induced by either blood PD-1$^{hi}$ CXCR5$^+$ cells or PD-1$^{hi}$ CXCR5$^-$ cells by ~90% (FIG. 6D).

SLAM family members, including SLAMF5 (CD84) and SLAMF6, and the downstream signaling adapter SAP, are expressed by Tfh cells and important for T-B cell interactions(25). Expression of SLAM, SLAMF5 and SLAMF6 were elevated on both PD-1$^{hi}$ CXCR5$^-$ and PD-1$^{hi}$ CXCR5$^+$ cells compared to PD-1$^-$ cells (FIG. 6E, FIG. 11A). Antibody blockade of SLAMF5, but not SLAMF6, completely abrogated the ability of PD-1$^{hi}$ CXCR5- T cells and PD-1$^{hi}$ CXCR5+ T cells to induce plasma cell differentiation or IgG production (FIG. 6F, FIGS. 11B-11C). Taken together, these data demonstrate that PD-1$^{hi}$ CXCR5$^-$ CD4$^+$ T cells potently promote B cell differentiation into antibody-secreting cells in vitro.

To further evaluate potential interactions in vivo, we examined the localization of PD-1$^{hi}$ CD4+ T cells in RA synovial tissue by immunofluorescence microscopy. Cells with bright PD-1 expression resided within small aggregates throughout seropositive RA synovium. PD-1$^{hi}$ cells co-localized with CD19+ B cells in multiple areas, including in regions that did not contain large organized infiltrates suggestive of ectopic lymphoid structures (FIGS. 6H-6I). Finally, we evaluated the frequency of circulating plasmablasts in seropositive RA patients before and after escalation of immunosuppressive therapy observed that the frequency of circulating plasmablasts decreased with treatment escalation, paralleling the reduction in PD-1$^{hi}$ CXCR5− CD4+ T cells (FIG. 6G compared to FIG. 2E).

Discussion

By integrating multiparametric cell phenotyping of activated T cells from affected tissues with transcriptomic and functional analyses, we identify a population of PD-1$^{hi}$ CXCR5$^-$ CD4$^+$ cells expanded in the joints and circulation of seropositive RA patients that displays potent B cell helper function. This is in contrast with the prevalent view that PD-1 expression is a marker of dysfunctional CD4+ T cells (26, 27). With characteristic expression of inflammatory chemokine receptors, PD-1$^{hi}$ CXCR5$^-$ T cells appear uniquely poised to support B cell responses within inflamed peripheral tissues. We suggest that these cells demonstrate a 'peripheral helper' T (Tph) cell phenotype, in contrast to CXCR5$^+$ 'follicular helper' T cells.

Rheumatoid synovium is often studded with T cell-B cell aggregates, which may support plasma cell differentiation within synovium (28-31). We hypothesize that Tph cells may be recruited to inflamed synovium via inflammatory chemokine receptors and produce IL-21 and CXCL13 locally to support B cell recruitment, plasma cell differentiation and autoantibody production. Actions of Tph cells may also provide a mechanism for the initiation of ectopic lymphoid structures in inflamed tissues, which would not be expected to readily recruit Tfh cells. PD-1$^+$ CD4$^+$ T cells also closely interact with B cells in kidneys of patients with lupus nephritis, although CXCR5 was not evaluated in this study(35). Here we extend these studies by detailing a comprehensive phenotype with which to identify Tph cells, demonstrating directly their potent B cell helper function, and providing a transcriptomic framework to understand their relationship to Tfh cells.

Several lines of evidence indicate major differences between Tph cells and Tfh cells. First, global transcriptomics analyses robustly separate Tph and Tfh cells, suggesting broad transcriptional differences. Second, Tph cells in both circulation and synovial fluid show increased expression of Blimp1, a potent negative regulator of Tfh cell development(36). Third, Tph cells express inflammatory chemokine receptors (CCR2, CX3CR1, CCR5) that are distinctly uncommon on Tfh cells(13). While Tph and Tfh cells demonstrated partial plasticity in CXCR5 expression in vitro, CCR2 expression remained restricted to Tph cells. Nonetheless, the Tph cell phenotype may represent an alternate functional state acquired by some Tfh cells. Alternatively, non-Tfh cells may acquire a Tph phenotype, perhaps favored in conditions of chronic antigen stimulation (12). In either case, identification of the Tph cell phenotype considerably expands the spectrum of B cell-helper T cells, such that both Tfh cells and Tph cells, which outnumber Tfh cells in circulation by 2-fold, should be considered in future mechanistic and biomarker development studies of antibody-associated diseases.

In summary, this description of an abundant population of PD-1$^{hi}$ tissue-directed B cell-helper T cells highlights the utility of integrating detailed cytometric assessments of human pathologic tissues with transcriptional and functional analyses. Further evaluation of PD-1$^{hi}$ Tph cells may advance mechanistic studies of autoimmune tissue inflammation, development of biomarkers for autoantibody-associated diseases, and design of novel therapeutic strategies to disrupt tissue T cell-B cell interactions. High expression of PD-1$^{hi}$ on Tph cells may also influence interpretation of the effects of therapeutic manipulation of the PD-1 pathway.

REFERENCES

1. Firestein G S. Rheumatoid arthritis in a mouse? Nat Clin Pract Rheumatol. 2009; 5(1):1.
2. Roep B O, Atkinson M, von Herrath M. Satisfaction (not) guaranteed: re-evaluating the use of animal models of type 1 diabetes. Nat Rev Immunol. 2004; 4(12):989-97.
3. Seok J, Warren H S, Cuenca A G, Mindrinos M N, Baker H V, Xu W, et al. Genomic responses in mouse models poorly mimic human inflammatory diseases. Proc Natl Acad Sci USA. 2013; 110(9):3507-12.
4. Casanova J L, Abel L, Quintana-Murci L. Human TLRs and IL-1Rs in host defense: natural insights from evolutionary, epidemiological, and clinical genetics. Annu Rev Immunol. 2011; 29:447-91.
5. Kugyelka R, Kohl Z, Olasz K, Mikecz K, Rauch T A, Glant T T, et al. Enigma of IL-17 and Th17 Cells in Rheumatoid Arthritis and in Autoimmune Animal Models of Arthritis. Mediators Inflamm. 2016; 2016:6145810.
6. Qin S, Rottman J B, Myers P, Kassam N, Weinblatt M, Loetscher M, et al. The chemokine receptors CXCR3 and CCR5 mark subsets of T cells associated with certain inflammatory reactions. J Clin Invest. 1998; 101(4):746-54.
7. James E A, Rieck M, Pieper J, Gebe J A, Yue B B, Tatum M, et al. Citrulline-specific Th1 cells are increased in rheumatoid arthritis and their frequency is influenced by disease duration and therapy. Arthritis Rheumatol. 2014; 66(7):1712-22.
8. Pitzalis C, Jones G W, Bombardieri M, Jones S A. Ectopic lymphoid-like structures in infection, cancer and autoimmunity. Nat Rev Immunol. 2014; 14(7):447-62.
9. Yu M, Cavero V, Lu Q, Li H. Follicular helper T cells in rheumatoid arthritis. Clin Rheumatol. 2015; 34(9):1489-93.
10. Maecker H T, McCoy J P, Nussenblatt R. Standardizing immunophenotyping for the Human Immunology Project. Nat Rev Immunol. 2012; 12(3):191-200.
11. Agata Y, Kawasaki A, Nishimura H, Ishida Y, Tsubata T, Yagita H, et al. Expression of the PD-1 antigen on the surface of stimulated mouse T and B lymphocytes. Int Immunol. 1996; 8(5):765-72.
12. Wherry E J, Kurachi M. Molecular and cellular insights into T cell exhaustion. Nat Rev Immunol. 2015; 15(8): 486-99.
13. Crotty S. Follicular helper CD4 T cells (TFH). Annu Rev Immunol. 2011; 29:621-63.
14. Amir el A D, Davis K L, Tadmor M D, Simonds E F, Levine J H, Bendall S C, et al. viSNE enables visualization of high dimensional single-cell data and reveals phenotypic heterogeneity of leukemia. Nat Biotechnol. 2013; 31(6):545-52.
15. Forster R, Schubel A, Breitfeld D, Kremmer E, Renner-Muller I, Wolf E, et al. CCR7 coordinates the primary immune response by establishing functional microenvironments in secondary lymphoid organs. Cell. 1999; 99(1):23-33.
16. DeGrendele H C, Estess P, Siegelman M H. Requirement for CD44 in activated T cell extravasation into an inflammatory site. Science. 1997; 278(5338):672-5.
17. Picelli S, Bjorklund A K, Faridani O R, Sagasser S, Winberg G, Sandberg R. Smart-seq2 for sensitive full-length transcriptome profiling in single cells. Nat Methods. 2013; 10(11):1096-8.
18. Chtanova T, Tangye S G, Newton R, Frank N, Hodge M R, Rolph M S, et al. T follicular helper cells express a distinctive transcriptional profile, reflecting their role as non-Th1/Th2 effector cells that provide help for B cells. J Immunol. 2004; 173(1):68-78.
19. Locci M, Havenar-Daughton C, Landais E, Wu J, Kroenke M A, Arlehamn C L, et al. Human circulating PD-1+CXCR3−CXCR5+ memory Tfh cells are highly functional and correlate with broadly neutralizing HIV antibody responses. Immunity. 2013; 39(4):758-69.
20. Weinstein J S, Lezon-Geyda K, Maksimova Y, Craft S, Zhang Y, Su M, et al. Global transcriptome analysis and enhancer landscape of human primary T follicular helper and T effector lymphocytes. Blood. 2014; 124(25):3719-29.
21. Kenefeck R, Wang C J, Kapadi T, Wardzinski L, Attridge K, Clough L E, et al. Follicular helper T cell signature in type 1 diabetes. J Clin Invest. 2015; 125(1):292-303.
22. Haringman J J, Smeets T J, Reinders-Blankert P, Tak P P. Chemokine and chemokine receptor expression in paired peripheral blood mononuclear cells and synovial tissue of patients with rheumatoid arthritis, osteoarthritis, and reactive arthritis. Ann Rheum Dis. 2006; 65(3):294-300.
23. Katschke K J, Jr., Rottman J B, Ruth J H, Qin S, Wu L, LaRosa G, et al. Differential expression of chemokine receptors on peripheral blood, synovial fluid, and synovial tissue monocytes/macrophages in rheumatoid arthritis. Arthritis Rheum. 2001; 44(5):1022-32.
24. Rot A, von Andrian U H. Chemokines in innate and adaptive host defense: basic chemokinese grammar for immune cells. Annu Rev Immunol. 2004; 22:891-928.
25. Cannons J L, Qi H, Lu K T, Dutta M, Gomez-Rodriguez J, Cheng J, et al. Optimal germinal center responses require a multistage T cell:B cell adhesion process involving integrins, SLAM-associated protein, and CD84. Immunity. 2010; 32(2):253-65.
26. Frederiksen J, Buggert M, Noyan K, Nowak P, Sonnerborg A, Lund O, et al. Multidimensional Clusters of CD4+ T Cell Dysfunction Are Primarily Associated with the CD4/CD8 Ratio in Chronic HIV Infection. PLoS One. 2015; 10(9):e0137635.
27. Hatachi S, Iwai Y, Kawano S, Morinobu S, Kobayashi M, Koshiba M, et al. CD4+ PD-1+ T cells accumulate as unique anergic cells in rheumatoid arthritis synovial fluid. J Rheumatol. 2003; 30(7):1410-9.
28. Takemura S, Braun A, Crowson C, Kurtin P J, Cofield R H, O'Fallon W M, et al. Lymphoid neogenesis in rheumatoid synovitis. J Immunol. 2001; 167(2):1072-80.
29. Pitzalis C, Kelly S, Humby F. New learnings on the pathophysiology of RA from synovial biopsies. Curr Opin Rheumatol. 2013; 25(3):334-44.
30. Humby F, Bombardieri M, Manzo A, Kelly S, Blades M C, Kirkham B, et al. Ectopic lymphoid structures support ongoing production of class-switched autoantibodies in rheumatoid synovium. PLoS Med. 2009; 6(1):e1.
31. Scheel T, Gursche A, Zacher J, Haupl T, Berek C. V-region gene analysis of locally defined synovial B and plasma cells reveals selected B cell expansion and accumulation of plasma cell clones in rheumatoid arthritis. Arthritis Rheum. 2011; 63(1):63-72.
32. Raptopoulou A P, Bertsias G, Makrygiannakis D, Verginis P, Kritikos I, Tzardi M, et al. The programmed death 1/programmed death ligand 1 inhibitory pathway is up-regulated in rheumatoid synovium and regulates peripheral T cell responses in human and murine arthritis. Arthritis Rheum. 2010; 62(7):1870-80.
33. Manzo A, Vitolo B, Humby F, Caporali R, Jarrossay D, Dell'accio F, et al. Mature antigen-experienced T helper cells synthesize and secrete the B cell chemoattractant CXCL13 in the inflammatory environment of the rheumatoid joint. Arthritis Rheum. 2008; 58(11):3377-87.
34. Kobayashi S, Murata K, Shibuya H, Morita M, Ishikawa M, Furu M, et al. A distinct human CD4+ T cell subset that secretes CXCL13 in rheumatoid synovium. Arthritis Rheum. 2013; 65(12):3063-72.
35. Liarski V M, Kaverina N, Chang A, Brandt D, Yanez D, Talasnik L, et al. Cell distance mapping identifies functional T follicular helper cells in inflamed human renal tissue. Sci Transl Med. 2014; 6(230):230ra46.
36. Johnston R J, Poholek A C, DiToro D, Yusuf I, Eto D, Barnett B, et al. Bcl6 and Blimp-1 are reciprocal and antagonistic regulators of T follicular helper cell differentiation. Science. 2009; 325(5943):1006-10.
37. Fletcher A L, Malhotra D, Acton S E, Lukacs-Kornek V, Bellemare-Pelletier A, Curry M, et al. Reproducible isolation of lymph node stromal cells reveals site-dependent differences in fibroblastic reticular cells. Front Immunol. 2011; 2:35.
38. Finck R, Simonds E F, Jager A, Krishnaswamy S, Sachs K, Fantl W, et al. Normalization of mass cytometry data with bead standards. Cytometry A. 2013; 83(5):483-94.
39. Finak G, Perez J M, Weng A, Gottardo R. Optimizing transformations for automated, high throughput analysis of flow cytometry data. BMC Bioinformatics. 2010; 11:546.
40. Bray N P, H.; Melsted, P.; Pachter, L. Near-optimal RNA-Seq quantification. arXiv. 2015; 1505:02710v2.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of detecting T peripheral helper (Tph) cells in a subject comprising:
   (i) obtaining a sample of cells from the subject;
   (ii) contacting the sample with:
      (a) an antibody specific for PD-1;
      (b) an antibody specific for CXCR5;
      (c) one or more antibodies each specific for a marker selected from the group consisting of: CCR2, CCR5 and CX3CR1; and
      (d) one or more antibodies each specific for a marker selected from the group consisting of: MHC Class II and ICOS; and
   (iii) immunodetecting Tph cells in the sample, wherein a Tph cell is characterized as having high expression of PD-1, low or no expression of CXCR5, expression of one or more of CCR2, CCR5 and CX3CR1, and expression of MHC Class II and/or ICOS.

2. The method of claim 1, wherein the subject has not been diagnosed with rheumatoid arthritis.

3. The method of claim 1, wherein the subject has or is at risk of developing rheumatoid arthritis.

4. The method of claim 1, wherein the subject has or is at risk of developing systemic lupus erythematosus (SLE).

5. The method of claim 1, wherein the subject has received a therapy.

6. The method of claim 5, wherein the therapy comprises an anti-inflammatory agent.

7. The method of claim 1, wherein the subject will receive a therapy.

8. The method of claim 7, wherein the therapy comprises an anti-inflammatory agent.

9. The method of claim 1, wherein the sample is a whole blood sample or mononuclear blood cell sample.

10. The method of claim 1, wherein the sample is a synovial fluid or tissue sample.

11. The method of claim 1, further comprising quantitating Tph cell number or frequency in the sample.

12. The method of claim 1, wherein the one or more antibodies of (d) comprise an antibody specific for MHC Class II and an antibody specific for ICOS.

13. The method of claim 1, wherein the one or more antibodies of (c) comprise an antibody specific for CCR2 and the one or more antibodies of (d) comprise an antibody specific for MHC Class II.

14. The method of claim 1, wherein the one or more antibodies of (c) comprise an antibody specific for CCR5 and the one or more antibodies of (d) comprise an antibody specific for MHC Class II.

15. The method of claim 1, wherein the one or more antibodies of (c) comprise an antibody specific for CX3CR1 and the one or more antibodies of (d) comprise an antibody specific for MHC Class II.

16. The method of claim 1, wherein the one or more antibodies of (c) comprise an antibody specific for CCR2 and the one or more antibodies of (d) comprise an antibody specific for ICOS.

17. The method of claim 1, wherein the one or more antibodies of (c) comprise an antibody specific for CCR5 and the one or more antibodies of (d) comprise an antibody specific for ICOS.

18. The method of claim 1, wherein the one or more antibodies of (c) comprise an antibody specific for CX3CR1 and the one or more antibodies of (d) comprise an antibody specific for ICOS.

* * * * *

SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1
cataggaagc tgggagcaag                                          20

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide

```
<400> SEQUENCE: 2
gccctccaat cagtcttctg                                          20

<210> SEQ ID NO 3
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 3
ctcttctgcc tgctgcactt tg                                       22

<210> SEQ ID NO 4
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 4
atgggctaca ggcttgtcac tc                                       22

<210> SEQ ID NO 5
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 5
agaactcaaa cctctggagg aag                                      23

<210> SEQ ID NO 6
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 6
gctgtctcag catattcaca c                                        21

<210> SEQ ID NO 7
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 7
gcatcgtttt gggttctctt g                                        21

<210> SEQ ID NO 8
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 8
agttccatta tccgctacat ctg                                      23

<210> SEQ ID NO 9
<211> LENGTH: 18
```

```
<212> TYPE: DNA
<213> ORGANISM: Artificial Sequence
<220> FEATURE:
<223> OTHER INFORMATION: Synthetic Polynucleotide

<400> SEQUENCE: 9
cgcatgtgaa ctccctgg                                                   18

<210> SEQ ID NO 10
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 10
tagatgcctt tctcttggag c                                               21

<210> SEQ ID NO 11
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 11
aggaaaccac cttccacaaa                                                 20

<210> SEQ ID NO 12
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 12
gaatcacatg aagggcatgt t                                               21

<210> SEQ ID NO 13
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 13
tctctgcttc tcatgctgct                                                 20

<210> SEQ ID NO 14
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 14
tcaagcttgt gtaatagacc tcca                                            24

<210> SEQ ID NO 15
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 15
```

```
ccaggatggt tcttagactc c                                              21

<210> SEQ ID NO 16
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 16
tttagcacga agctctccga t                                              21

<210> SEQ ID NO 17
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 17
ccgtcctctc ccgagttttt                                                20

<210> SEQ ID NO 18
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 18
tgctggggct tccaaaatgt                                                20

<210> SEQ ID NO 19
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 19
gtttccggca ccttcagact                                                20

<210> SEQ ID NO 20
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 20
ctggcttttg tgacggaaat                                                20

<210> SEQ ID NO 21
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 21
tggcaaacag gactcatctg                                                20

<210> SEQ ID NO 22
<211> LENGTH: 20
<212> TYPE: DNA
<213> ORGANISM: Artificial Sequence
```

```
<220> FEATURE:
<223> OTHER INFORMATION: Synthetic Polynucleotide

<400> SEQUENCE: 22
ctgtttctcc aggtcttcgc                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 23
gctatttgct gagggacagc                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 24
tgtctgggac actcggtatg                                              20

<210> SEQ ID NO 25
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 25
aacttcttgt gtggtattgt cgg                                          23

<210> SEQ ID NO 26
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 26
tctcagtgct cggttgcttt                                              20
```